(12) United States Patent
Spivack et al.

(10) Patent No.: US 8,846,350 B2
(45) Date of Patent: Sep. 30, 2014

(54) MICRORNA AFFINITY ASSAY AND USES THEREOF

(75) Inventors: Simon D. Spivack, Sleepy Hollow, NY (US); Miao Shi, Woodside, NY (US); Weiguo Han, Albany, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/500,083

(22) PCT Filed: Oct. 18, 2010

(86) PCT No.: PCT/US2010/002771
§ 371 (c)(1),
(2), (4) Date: Jun. 27, 2012

(87) PCT Pub. No.: WO2011/056186
PCT Pub. Date: May 12, 2011

(65) Prior Publication Data
US 2012/0264619 A1 Oct. 18, 2012

Related U.S. Application Data

(60) Provisional application No. 61/279,803, filed on Oct. 26, 2009.

(51) Int. Cl.
| | | |
|---|---|---|
| C12P 19/34 | (2006.01) |
| C07H 21/02 | (2006.01) |
| C12Q 1/68 | (2006.01) |
| C12N 15/11 | (2006.01) |

(52) U.S. Cl.
CPC ............ C12N 15/111 (2013.01); C12Q 1/6858 (2013.01); C12Q 1/6806 (2013.01); C12Q 1/6827 (2013.01); C12N 2310/141 (2013.01); C12N 2320/11 (2013.01)
USPC ........................................ 435/91.3; 536/23.1

(58) Field of Classification Search
None
See application file for complete search history.

(56) References Cited

U.S. PATENT DOCUMENTS

| | | | |
|---|---|---|---|
| 2005/0214300 A1* | 9/2005 | Venetsanakos | 424/155.1 |
| 2005/0221383 A1* | 10/2005 | Liew et al. | 435/7.1 |
| 2006/0024658 A1* | 2/2006 | Miles et al. | 435/4 |
| 2007/0059739 A1* | 3/2007 | Lao | 435/6 |
| 2009/0053775 A1* | 2/2009 | Dahl et al. | 435/91.51 |
| 2010/0297750 A1* | 11/2010 | Natsume et al. | 435/320.1 |
| 2011/0144914 A1* | 6/2011 | Harrington et al. | 702/19 |

OTHER PUBLICATIONS

Saba & Booth in "Target labeling for the detection and profiling of microRNAs expressed in CNS tissue using microarrays" (BMC Biotechnology: 2006, vol. 6:47, published Dec. 12, 2006, pp. 1-15 of attached article).*
Wakiyama M et al., entitled "Let-7 microRNA-mediated mRNA deadenylation and translational repression in a mammalian cell-free system," Genes Dev, Aug. 2007 vol. 21, No. 15, pp. 1857-1862.
Ryder U et al., entitled "Sequence-specific affinity selection of mammalian splicing complexes," Nucl Acids Res, Dec. 1990, vol. 18, No. 24, pp. 7373-7379.
Shi M et al., entitled "MicroRNA affinity assay," AACR 101st Annual Meeting, presented on Apr. 19, 2010, Abstract 2021, abstract only.
Vo N K et al., entitled "Affinity purification of microRNA-133a with cardiac transcription factor, Hand2," Proc Nat Acad Sci ePub, Oct. 25, 2010, vol. 107, No. 45, pp. 19231-19236.
Nonne N et al., entitled "Tandem affinity purification of miRNAs (TAP-Tar)," Nucl Acids Res, 2010, vol. 38, No. 4, pp. e20 1-5.
PCT International Search Report dated Feb. 11, 2011 in connection with PCT International Patent Application No. PCT/US2010/002771, 5 pages.
PCT Written Opinion of the International Searching Authority dated Feb. 11, 2011 in connection with PCT International Patent Application No. PCT/US2010/002771, 4 pages.

* cited by examiner

*Primary Examiner* — Catherine Hibbert
(74) *Attorney, Agent, or Firm* — Amster, Rothstein & Ebenstein LLP

(57) ABSTRACT

The present invention provides methods and kits for determining which microRNAs bind to a target mRNA where the methods comprise the steps of (a) creating a bait sequence from the target mRNA, where the bait sequence comprises a label that binds to a binding agent; (b) adding a mixture of microRNAs to the bait sequence; (c) separating the microRNAs that bind to the bait sequence from those microRNAs that do not bind; and (d) identifying the microRNAs that bind to the bait sequence, wherein the microRNAs identified are those that bind to the target mRNA.

18 Claims, 12 Drawing Sheets

MICRORNA AFFINITY ASSAY AND USES THEREOF

CROSS-REFERENCE TO RELATED APPLICATIONS

This application is a U.S. national stage entry under 35 U.S.C. §371 of PCT International Patent Application No. PCT/US2010/002771, filed Oct. 18, 2010, and claims priority to U.S. Provisional Patent Application No. 61/279,803, filed on Oct. 26, 2009, the contents of which are incorporated herein by reference in their entirety.

STATEMENT OF GOVERNMENT SUPPORT

This invention was made with government support under grant numbers CA106186 and CA121068 awarded by the National Institutes of Health. The government has certain rights in the invention.

FIELD OF THE INVENTION

The present invention relates to assays and kits for the verification of binding by microRNA to given mRNA.

BACKGROUND OF THE INVENTION

MicroRNAs (also referred to herein as "miRNA"s) function in gene regulation by regulating mRNA transcript stability and mRNA translation to proteins. A miRNA is complementary to a part of one or more messenger RNAs (mRNAs). Animal miRNAs are usually complementary to a site in the 3' UTR where the microRNAs partially base pair and inhibit protein translation of the target mRNA. MicroRNAs that are partially complementary to the target can also speed up deadenylation, causing mRNAs to be degraded sooner. For partially complementary microRNA to recognise their targets, the nucleotides 2-7 of the miRNA ('seed region'), generally have to be highly complementary. MiRNAs occasionally also causes DNA methylation of promoter sites and therefore affecting the expression of targeted genes. MiRNAs function in association with a complement of proteins collectively termed the miRNP. Human miRNPs contain eIF2C2 (also known as Argonaute 2), DDX20, GEMIN4 and microRNA.

Animal microRNAs target particular developmental genes. In contrast, genes involved in functions common to all cells, such as gene expression, have very few microRNA target sites, and seem to be under selection to avoid targeting by microRNAs.

As of 2002, miRNAs had been confirmed in various plants and animals, including *C. elegans*, human and the plant *Arabidopsis thaliana*. There has been production of microarrays (e.g., dubbed MMChips) containing all the known miRNAs for human, mouse, rat, dog, *C. elegans* and *Drosophila*. Agilent and other firms have subsequently commercialized human miRNA microarrays.

MicroRNA expression can be quantified by modified RT followed by qPCR, or profiled against a database describing thousands of known miRNAs using microarray technology. The activity of a miRNA can be experimentally inhibited using a locked nucleic acid oligo, a Morpholino oligo or a 2'-O-methyl RNA oligo. MicroRNA maturation can be inhibited at several points by steric-blocking oligos. The miRNA target site of an mRNA transcript can also be blocked by a steric-blocking oligo. Additionally, a specific miRNA can be silenced by a complementary antagomir.

MicroRNAs regulate mRNA transcript stability and mRNA translation to proteins. The binding of a specific microRNA to a given target mRNA is difficult to directly affirm using currently available techniques. Using conventional informatics approaches, publically available sequence software is notoriously unreliable, exemplified in that each program differs dramatically in prediction of binding of individual microRNAs to a given mRNA transcript. This is in part due to the tendency of short microRNA oligos to have high homology to many transcriptome and genomic sequences as well as the subtle sequence differences among microRNAs of one or very few bases. Experimentally, microRNAs can bind cDNA oligomers on a spotted microarray, or alternately a particular cDNA, with a number of mismatches; these cDNA-based methods are both non-specific, and do not measure the interaction of biological interest (microRNA:mRNA binding). The binding of a specific microRNA to a given target mRNA is at the crux of transcript stability and translational regulation. Identification of microRNAs which bind to a given target mRNA will allow the use of microRNAs for targeted repression of mRNA translation and degradation of mRNAs, thereby affecting gene expression. Specific microRNA-mRNA binding is very difficult to affirm using currently available techniques. Informatics approaches are of variable reliability. Experimental approaches are largely non-existent. The present invention addresses this need.

SUMMARY OF THE INVENTION

The present invention provides a method for determining which microRNAs bind to a given target mRNA comprising the steps of (a) creating a bait sequence from the target mRNA, where the bait sequence comprises a label that binds to a binding agent; (b) adding a mixture of microRNAs to the bait sequence; (c) separating the microRNAs that bind to the bait sequence from those microRNAs that do not bind; and (d) identifying the microRNAs that bind to the bait sequence, wherein the microRNAs identified are those that bind to the target mRNA.

The present invention also provides a kit for determining which microRNAs bind to a given target mRNA comprising reagents for (1) creating a bait from the target mRNA; (2) separating the microRNAs that bind to the bait sequence from those microRNAs which do not; and (3) identifying the microRNAs that bind to the bait sequence, wherein the microRNAs identified are those which bind to the target mRNA.

DETAILED DESCRIPTION OF THE INVENTION

Figure 1:
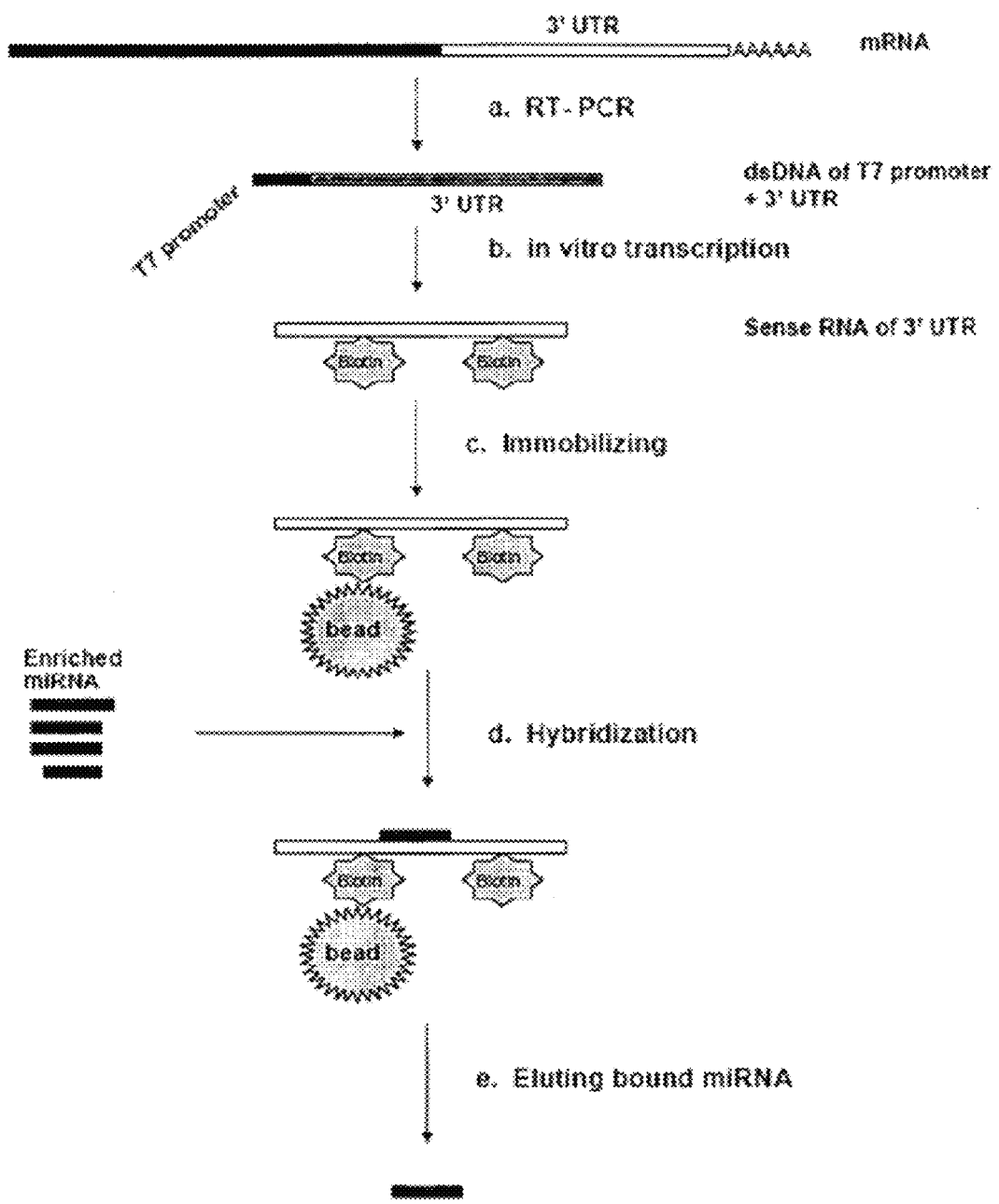
FIG. 1. microRNA pull-down. a. RT-PCR—cRNA target sequence is generated by, first, reverse transcription to synthesize cDNA from mRNA, and then PCR to synthesize double-stranded 3'UTR with T7 promoter at its 5' end from cDNA. b. In vitro transcription—use T7 RNA polymerase to synthesize 3'UTR_RNA in vitro. Because NTP mixture contains biotin-16-UTP, the synthesized RNA contains biotin. c. Immobilizing—immobilize the biotinylated RNA to the streptavidin magnetic beads and wash the beads for removing the non-specifically bound RNA. d. Hybridization—add enriched microRNAs to the beads, and hybridize microRNAs and 3'UTR_RNA, wash the beads to remove the non-specifically bound microRNAs. e. Eluting bound microRNA—elute specifically bound microRNAs.

The present invention provides a method for determining which microRNAs bind to a given target mRNA comprising the steps of (a) creating a bait sequence from the target mRNA, where the bait sequence comprises a label that binds to a binding agent; (b) adding a mixture of microRNAs to the bait sequence; (c) separating the microRNAs that bind to the bait sequence from those microRNAs that do not bind; and (d) identifying the microRNAs that bind to the bait sequence, wherein the microRNAs identified are those that bind to the target mRNA.

The present invention also provides a kit for determining which microRNAs bind to a target mRNA comprising reagents for (1) creating a bait from the target mRNA; (2) separating the microRNAs that bind to the bait sequence from those microRNAs which do not; and (3) identifying the microRNAs that bind to the bait sequence, wherein the microRNAs identified are those which bind to the target mRNA. The kit may also include instructions for use.

mRNA is messenger RNA transcribed from DNA which carries coding information. This information can be translated to a polymer of amino acids. microRNA is a single strand of RNA of 10-50 nucleotides. More preferably, it is 15-30 nucleotides in length. Most preferably it is 21-23 nucleotides in length. microRNAs are partially complementary to one or more mRNAs and down-regulate gene expression. ss RNA is a single strand RNA. cDNA (complimentary DNA) is single stranded DNA transcribed from RNA. PCR (polymerase chain reaction) is a technique to amplify a single or a few copies of a particular DNA sequence by several orders of magnitude. Transcription is the synthesis of RNA from DNA where the DNA nucleotide sequence information is transferred into RNA nucleotide sequence information. Reverse transcription is the synthesis of single stranded cDNA from RNA. Sequencing is the determination of the order of nucleotide bases in a molecule of DNA or RNA. 3'UTR is the three prime untranslated region of RNA which follows the coding region of RNA. In mRNA, the 3'UTR region may be, for example, a regulatory sequence such as polyadenylation signal, a binding site for proteins (which affect the stability and location of the mRNA in the cell), or a binding site for microRNAs or other RNA interference. 3'UTR_RNA is RNA with a three prime untranslated region. polyA, or poly(A) tail, is a stretch of multiple adenosine monophosphates. Addition of polyA is a step in the maturation of RNA for translation. PolyA is located at the 3' end of RNA, after the three prime untranslated region.

A bait sequence is a nucleotide sequence which corresponds to the nucleotide sequence of the target mRNA. Such a bait sequence will be able to Watson-Crick base pair with the microRNAs that specifically bind to the target mRNA. The bait sequence can be any such sequence known in the art, for example, 3'UTR_RNA, 5'UTR_RNA, mRNA fragment, mRNA, cDNA, or microRNA. Preferably, the bait sequence is a 3'UTR_RNA. The bait sequence can be made by any method known in the art, for example, direct synthesis of the bait sequence or PCR and in vitro transcription of the target mRNA. For example, the bait sequence 3'UTR_RNA can be created by any method known in the art, such as by creating a double-stranded 3'UTR from the target mRNA and then synthesizing 3'UTR_RNA from that double-stranded 3'UTR. Preferably, reverse transcription is used to synthesize cDNA from the target mRNA and PCR is then used to generate double-stranded 3'UTR. Preferably, transcription, and most preferably in vitro transcription, is used to synthesize 3'UTR_RNA from the double-stranded 3'UTR. Any reagents known in the art can be used for reverse transcription, such as a mixture of dNTPs, URT primer, buffer, DTT, and SuperScript® III RT. Any reagents known in the art can be used for PCR, such as a mixture of GoTaq Buffer, $MgCl_2$, dNTP, primers, and DNA polymerase. Any reagents known in the art can be used for transcription or in vitro transcription. For example, an RNA labeling mix and transcription buffers may be used with in vitro transcription. The labeling mix may include any label known in the art, such as biotin or digoxigen.

The bait sequence can be labeled by any method known in the art, for example, incorporation during sequence synthesis, ligating a RNA with biotin, 3'end labeling, or 5'end labeling. Labeled bait sequence can be immobilized to a substrate. This can be done by any method known in the art, including the use of a binding agent or by affinity interaction. A binding agent is a molecule or compound that preferentially retains the label or binds tightly to the label with a high dissociation constant. Any binding agent—label combination known in the art can be used, for example, digoxigenin or biotin and streptavidin. Therefore, in one embodiment, the ribonucleoside triphosphate (NTP) solution used during in vitro transcription contains biotin-16-UTP, and therefore the synthesized bait sequence contains biotin. Most preferably, the in vitro transcription of 3'UTR_RNA is done in the presence of biotin-16-UTP, resulting in biotinylated 3'UTR_RNA. The biotinylated bait sequence can be immobilized on a substrate containing steptavidin. The substrate on which the bait sequence are immobilized can be any substrate known in the art, including beads, gel, or an elution column. Preferably, the substrates are beads, for example glass or magnetic beads. Most preferably the beads are magnetic.

In order to determine which microRNAs bind to the target mRNA, a mixture of the microRNAs being studied is added to the bait sequence. The microRNAs which bind to the target mRNA will hybridize with the bait sequence. Those microRNAs which will not bind to the target mRNA will not hybridize with the bait sequence. The microRNAs and bait sequence can be hybridized by any method known in the art such as by adding hybridization buffer to the microRNA—bait sequence mixture and incubating.

The microRNAs which hybridize to the bait sequence can then be separated from those which do not by any means known in the art, such as by elution or the application of a magnetic field. As an example, if the bait sequence is labeled, the bait sequence, and the microRNAs which hybridize to it, will be retained in an elution column containing streptavidin while those microRNAs which do not hybridize to the bait sequence, and therefore which do not bind to the target mRNA, are not retained. In another example, the bait sequence is biotinylated and is immobilized on magnetic beads containing streptavidin. The bait sequence and the microRNAs which hybridize to it can then be separated from those microRNAs which do not by the application of a magnetic field. The microRNAs which do not bind to the target mRNA, and therefore do not bind to the bait sequence, can then be removed from the magnetic beads containing the bait sequence and the hybridized microRNAs by any method known in the art, such as by washing the beads.

After the microRNAs which did not hybridize with the bait sequence are removed, the microRNAs that did hybridize with the bait sequence can be released from the bait sequence by any method known in the art such as by washing the hybridized bait sequence—microRNAs with RNaseOUT, increasing solution temperature, or adding denaturing buffer.

The microRNAs that are released from the bait sequence are those which bind to the target mRNA. These released microRNAs can be identified by any method known in the art, such as by RT-PCR or sequencing. Any sequencing technology known in the art can be used, for example, for direct dideoxynucleotide sequencing without cloning or indirect sequencing with cloning. Any reagents known in the art for directly sequencing the microRNAs can be used. Preferably, the released microRNAs are indirectly sequenced by synthesizing cDNA from the released microRNAs, and then cloning and sequencing the cDNA. cDNA can be synthesized by any means known in the art, including reverse transcription. The cDNA cloning can be done by any method known in the art, for example, PCR. Any reagents known in the art can be used for reverse transcription, such as a mixture of dNTPs, URT primer, buffer, DTT, and SuperScript® III RT. Any reagents known in the art can be used for PCR, such as a mixture of GoTaq Buffer, MgCle, dNTP, primers, and DNA polymerase.

The released microRNAs may undergo preparatory steps prior to direct sequencing or cloning and sequencing. These steps can be any small RNA sequencing technology known in the art, for example, 3' polyA tailing, 5' ligation tagging, reverse transcription and PCR amplification or 3' ligation tagging, 5' ligation tagging, reverse transcription and PCR amplification. Most preferably, prior to synthesizing cDNA from the released microRNAs, RNA 5'polyphosphatase digestion is be used to remove the γ and β phosphotases from the 5'end of the released microRNAs, and polyA is added at the 3'end of the released microRNAs, and T4 RNA ligase is used to ligate ss RNA linker to the 5' end of the microRNAs before reverse transcription and PCR amplification. Any reagents for RNA 5'polyphosphatase digestion known in the art can be used, such as a mixture of phosphatases and reaction buffer. Any reagents for 3' polyA tailing known in the art can be used such as a mixture of reaction buffer, $MnCl_2$, ATP, and an enzyme. Any reagents for ligation tagging of either the 3' or 5' can be used, such as a mixture of ligation linker (3' or 5'), RNA ligase buffer, ATP, DTT, and T4 RNA ligase.

In a preferred embodiment, a biotinylated 3'UTR_RNA is created from the target mRNA by creating a double-stranded 3'UTR from the target mRNA via reverse transcription and PCR, and in vitro synthesis of 3'UTR_RNA from the 3'UTR. Preferably, the biotinylated 3'UTR_RNA is immobilized on streptavidin magnetic beads and is then mixed with microRNAs. Preferably, the microRNAs that do not bind to the 3'UTR_RNA are then removed and the microRNAs that bind to the 3'UTR_RNA are then released from the 3'UTR_RNA. Preferably, the released microRNAs are then identified by undergoing RNA 5'polyphosphatase digestion, 3'polyA tailing, 5' ligation tagging, reverse transcription of the released microRNAs into cDNA, PCR amplification, and cloning and sequencing of the cDNA.

In a preferred embodiment, the reagents for the kit to determine which microRNAs bind to a given target mRNA comprise a mixture of dNTPs, URT primer, buffer, DTT, and SuperScript® III RT for reverse transcription; a mixture of GoTaq Buffer, $MgCl_2$, dNTP, primers, and DNA polymerase for PCR; RNA labeling mix (NTP solution containing biotin-16-UHP) and transcription buffers for in vitro transcription; a mixture of phosphatases and reaction buffer for 5' polyphosphatase digestion; a mixture of reaction buffer, $MnCl_2$, ATP, and an enzyme for 3' polyA tailing; a mixture of ligation linker (3' or 5'), RNA ligase buffer, ATP, DTT, and T4 RNA ligase for 5' ligation tagging; and a mixture of dNTPs, URT primer, buffer, DTT, and SuperScript® III RT for cDNA cloning.

The sequence of the cDNA obtained after sequencing is the cDNA sequence for the microRNAs which bind to the target mRNA. The microRNAs which did not bind to the bait sequence are those microRNAs which do not bind to the target mRNA. Therefore, this method can be used both to determine which microRNAs in mixture of known microRNAs or a mixture of unknown microRNAs bind to the target mRNA. If the mixture of microRNAs is known, this method can also be used to determine which microRNAs will not bind to a target mRNA, or series of mRNAs.

Experimental Details

Certain materials and steps have been used herein solely for the purpose of describing the current best mode and are not to be taken as limitations on the present invention. The invention includes any material or steps which achieves a similar overall result.

Methods and Materials

Detailed microRNA pull-down protocol: Prepare biotinylated-3'UTR_RNA before beads operation, for example, by following the 4 step procedure outlined below. (1) Use RT-PCR to produce ds 3'UTR_DNA with T7 promoter (for example, 5'-TAATACGACTCACTATAGGG-3' (SEQ ID NO:1)) via (a) reverse transcription and (b) PCR amplification. Because the forward primer contains T7 promoter at its 5' end, ds 3'UTR_DNA contains T7 promoter at its 5' end. (2) Use in vitro transcription to synthesize 3'UTR_RNA with biotin. For example by using 200 ng TCF8_3'UTR PCR products, 2 µl 10× Biotin RNA labeling mix, 2 µl 10× transcription buffer, and RNase-free water to final volume of 20 µl and then mixing or briefly centrifuging and incubating (preferably at 37° C. for 2 hours). Because NTP contains biotin-16-UTP, the synthesized RNA contains biotin. (3) DNase I digestion by, for example, adding 5 µl DNase I (RNase-free) to the above reaction and incubating at 37° C. for 2 hours. (4) RNA clean-up and quantification by, for example, using QIAGEN RNA kit to clean the RNA, eluting with 50 µl elution buffer, and using NanoDrop to measure RNA concentration.

Beads operation procedure: (1) Resuspend beads, such as Dynabeads® MyOne™ Streptavidin T1, and pipet 100 µl of beads to a test tube. (2) Separate the beads out by, for example, placing the tube on a magnet for 1-2 minutes and removing the supernatant. (3) Wash the beads completely by, for example first washing the beads three times with 100 µl of 1× B&W buffer (1M NaCl, 5 mM Tris (pH7.5), 0.5 mM EDTA), then washing the beads twice in 100 µl of solution A (0.1M NaOH, 0.05M NaCl) for 2 min, then washing the beads once in 100 µl of solution B (0.1 M NaCl), and finally washing the beads seven times with 100 µl of 1× B&W buffer. (4) Resuspend the beads, for example, in 100 µl of 2× B&W buffer (2M NaCl, 10 mM Tris (pH7.5), 1 mM EDTA). (5) Pipet 3 ug biotinylated-3'UTR_RNA to a test tube and adjust the volume to 100 µl with RNase-free water. (6) Incubate at 65° C. for 5 minutes and cool immediately, for example, on ice. (7) Take 100 µl of the washed and resuspended beads and add 100 µl of the incubated and cooled RNA solution. (8) Incubate for 30 minutes at room temperature, using gentle rotation (such as that by hand). (9) Separate out the beads, for example, by placing the tube on a magnet and removing the supernatant. (10) Wash three times with 100 ul of 7 M urea (It is important to incubate the sample at 65° C. for 2 min before removing the supernatant). (11) Wash three times with 100 ul of 1× B&W buffer and remove the supernatant. (12) Pipette 1.6 ug miRNAs (column-purified from cell total RNA, nanodrop spectroscopy used to measure concentration) to a PCR tube. When testing using know miRNA, use 3.2 ng each of a synthesized pool of miRNA. (13) Preheat 33 µl of 3× miRNA hybridization buffer to 65° C. and to the miRNAs, add it along with x µl $H_2O$ to a final volume of 100 µl. (14) Incubate at 95° C. for 2 minutes and let cool to room temperature. (15) Add this miRNA solution to the beads. (16) Hybridize, for example at 35° C. for 30 minutes using gentle rotation such as shaking by hand once every 20 seconds and shaking by vortex once every 5 minutes. (17) Separate out the beads, for example, by placing the tube on a magnet and removing the supernatant. Keep the supernatant (these are "unbound miRNAs"). (18) Precipitate unbound miRNAs by mixing 100 µl of unbound miRNA solution, 34 µl of 1M NaCl, 2 µl of 20 mg/µl glycogen, and 136 µl of 2-propanol. (19) Incubate at −20° C. for 2 hours and then centrifuge at 14000 rpm for 20 minutes at 4° C. (20) Wash the pellet once with 70% ethanol and dissolve in 100 µl $H_2O$. (additional "unbound miRNA"). (21) Wash the beads completely by, for example first washing the beads three times at room temperature with 100 µl of 1×SSC/0.1% SDS, then washing the beads three times at room temperature with 100 µl of 0.5×SSC, and finally washing the beads three times at 42° C. with 100 µl of 0.5×SSC. (22) Resuspend the beads in 100 µl of $H_2O$. (23) Incubate the bead solution at 65° C. for 2 minutes and separate the beads immediately for example, by placing on a magnet. (24) Transfer the supernatant to a new tube and keep it at −20° C. (these are the "released miRNA").

Detailed microRNA cloning protocol: The six steps of this procedure include (a) RNA 5' polyphosphatase treatment, (b) 3' polyA tailing, (c) 5' ligation tagging, (d) reverse transcription (using URT primer), (e) PCR amplification, and (f) cloning and sequencing.

(a) RNA 5' polyphosphatase treatment. To 1 µl RNA 5' polyphosphatase (from Epicentre Biotechnologies) add 17 µl of the released miRNAs and 2 µl 10× reaction buffer for a total volume of 20 µl. Incubate at 37° C. for 30 minutes.

(b) 3' polyA tailing. Add together 10 µl 5× reaction buffer (from a polyA tailing kit), 4 µl 25 mM $MnCl_2$, 2 µl 100× diluted ATP, 1 µl enzyme (from a polyA tailing kit), 20 µl RNA solution from the RNA 5' polyphosphatase treatment, and 13 µl water for a total volume of 50 µl. Incubate at 37° C. for 30 minutes. Perform a phenol-chloroform extraction by adding 50 µl water to the reaction solution and using 25 ppv phenol:24 ppv chlorofom:1 ppv isoamyl alcohol to extract it and transfer the aqueous phase to a new tube. Back-extract the phenol-chloroform phase with 100 µl water. Collect the aqueous phase and combine it with the aqueous phase from the first extraction. Extract the combined aqueous material with 200 µl 24:1. Transfer the aqueous phase to a new 1.5 ml tube. Precipitate the RNA in the solution: (1) add 2 µl glycogen (20 mg/µl), 1/10 volume (20 µl) 3M NaAc (pH 5.2) and 2.5 volumes (500 µl) −20° C. ethanol; (2) mix briefly by, for example, inversion or vortex; (3) incubate at −80° C. for 30 minutes; (4) centrifuge at 4° C. at full speed (about 20,000 g) for 20 minutes; (5) pour off supernatant; (6) wash the pellet with 70% ethanol; (7) dry pellet completely; and (8) dissolve the pellet in 10 µl $H_2O$.

(c) Ligation of M.R.S. miRNA cloning linker. The sequence for 5' M.R.S. miRNA cloning linker (obtained from IDT) is 5'-TGGAATrUrCrUrCrGrGrGrCrArCr-CrArArGrGrU-3' (SEQ ID NO:2) (linker is a DNA/RNA hybrid. "r" before the nucleotide denotes an RNA base). Dissolve 1 nM of the linker in 20 µl $H_2O$ for a final concentration of 50 uM. At room temperature, to 1 µl (50 nM) of the M.R.S. cloning linker add: 10 µl purified RNA from the polyA tailings, 1 µl 10×RNA ligase buffer, 1 µl 2 mM ATP, 2 µl 0.1M DTT, 1 µl T4 RNA ligase, and 4 µl $H_2O$ for a total volume of 20 µl. Incubate at room temperature for 2 hours, and then heat at 65° C. for 10 minutes to inactivate the T4

RNA ligase. Following inactivation, add 80 μl H₂O, 2 μl glycogen (20 mg/μl), 1/10 volume (10 μl) 3M NaAc (pH 5.2), 2.5 volumes (250 μl) −20° C. ethanol and mix briefly by inversion or vortex. Incubate at −80° C. for 30 minutes and then centrifuge at 4° C. at full speed (about 20,000 g) for 20 minutes. Pour off supernatant, wash the pellet with 70% ethanol, dry pellet completely, and then dissolve the pellet in 10 μl H₂O.

(d) Reverse Transcription. The URT primer sequence is 5'-AACGAGACGACGACA-GACTTTTTTTTTTTTTTTTTTTTTTTV-3' (SEQ ID NO:3). In an RNase-free tube add 10 μl of the recovered linked RNA from the above step, 1 μl dNTPs (10 mM), 1 μl URT primer (10 uM), and 2 μl of water for a total volume of 14 μl. Incubate at 65° C. for 5 minutes and then cool immediately, for example, by placing on ice. Add 4 μl 5× First Strand Buffer, 1 μl 0.1M DTT, and 1 μl SuperScript® III RT (200 U/μl) for a total volume of 20 μl. Incubate at 50° C. for one hour, and then 70° C. for 15 minutes. This reaction can be stored at −20° C. until needed.

(e) PCR amplification. 5' Linker 5'-TGCAATrUrCrUrCr-GrGrGrCrArCrCrArArGrGrU-3' (SEQ ID NO:2). Primer sequence on the 5' linker PCR for: 5'-TGGAAT-TCTCGGGCACC-3' (SEQ ID NO:4) Tm: 55.0° C. URT sequence 5'-AACGAGACGACGACA-GACTTTTTTTTTTTTTTTTTTTTTTTV-3' (SEQ ID NO:3). Primer sequence on the URT U60: 5'-AACGAGACGACGA-CAGACTTT-3' (SEQ ID NO:5). PCR fragment size about 83 bp. In order to get linear PCR amplification, determine the minimum PCR cycle. Because different PCR cycle numbers need more time, use different dilutions to substitute them. Dilute the ligation products to 1/10, 1/30, 1/100, 1/300, 1/1000 (run one or all dilutions for quality control). The following mixture is prepared: 10 μl 5× colorless GoTaq buffer, 4 μl 25 mM MgCl₂, 0.5 μl 10 mM dNTP, 1 μl 10 uM primer, 1 μl 10 uM primer2, 0.25 μl (5 U/μl) GoTaq DNA polymerase, and 31.25 μl water for a total volume of 48 μl. Take 24 μl of the mixture with 1 μl of DNA template in each tube for each dilution being run. An example of PCR conditions is (1) 94° C. at 2 minutes, (2) 94° C. for 30 seconds, (3) 57° C. for 30 seconds, (4) 72° C. for 30 seconds, (5) repeat steps (1)-(4) for 20 cycles (cycles can be adjusted to 22 or 25 cycles to obtain more PCR products), and (6) 72° C. for 5 minutes. Run 6% PAGE gel. For linear application, choose the minimum dilution as PCR template. Based on the upper conditions, enough PCR products should be produced for cloning and sequencing.

(f) Conventional cloning and sequencing.

Results and Discussion

The invention provides a specific microRNA affinity based pull-down assay, which enables quantitative prediction of binding affinity of a given microRNA(s) to a given mRNA transcript sequence, with confidence. The binding assay can be used for microRNA discovery, and/or for confirmation of binding of a given mRNA, to a particular target mRNA sequence. Standard molecular biology instrumentation is sufficient to carry out the assay. The invention is completely different from extant technologies in that it assays microRNA:mRNA interaction directly, and qualitatively, without the assumptions informatics, and the non-specific annealing and qualitative nature inherent to a spotted cDNA microarray.

Example 1

Isolate Specific microRNAs to Target the Partial 3'UTR of TCF8 from a Synthesized microRNA Pool 200 family microRNAs can bind to the partial 3'UTR of 3'UTR of TCF8. The invention was used to isolate 200 family microRNAs from many synthesized microRNA mix. The protocol detailed above was utilized with the following special items:

During microRNA pull-down: (1) the forward primer for PCR amplification of TCF8_3'UTR was 5'-TAATACGACT-CACTATAGGGAGAGAAACTGAAACACTGGGAC-3' (SEQ ID NO:6) (5'-TAATACGACTCACTATAGGG-3' (SEQ ID NO:1) is T7 promoter); (2) the reverse primer is 5'-GGAGAACCAATTGCATCTCTAC-3' (SEQ ID NO:7); and (3) the synthesized microRNA mix pool includes miR-200c, miR-200b, miR-429, miR-9, miR-10a, miR-20a, miR-34a, miR-100, miR-140-5P, miR-144, miR-802, miR-1234.

After microRNA pull-down, use microRNA realtime PCR to check microRNA quantity. (1) PolyA tailing: using Ambion polyA tailing kit (Cat. No. AM1350), dilute ATP to 100× and prepare master mix (three separate times) of 5 μl 5× buffer, 2 μl 25 mM MnCl₂, 1 ATP(diluted), 0.5 μl Enzyme, 6.5 μl H₂O. Mix 15 μl of mater mix with 10 μl each original microRNA, unbound microRNA, and released microRNAs. Incubate at 37° C. for 30 mins. (2) Reverse transcript for polyA tailed RNA. Prepare 3 batches of master mix A containing 1 μl URT (100 uM), 1 μl H₂O, and 1 μl dNTP (10 uM each) and mix each batch with 10 μl RNA-polyA (original, unbound, and released). Incubate the reaction at 65° C. for ten minutes, and then at 4° C. for 1 minute. Prepare 3 batches of master mix B containing 4 μl 5× first-strand buffer, 1 μl DTT, 1 μl H₂O, and 1 μl SSIII. Add one batch of master mix B to each batch of master mix A for a final volume of 20 μl. Incubate at 25° C. for 5 minutes, at 50° C. for 50 minutes, 70° C. for 15 minutes, and hold at 4° C. (3) Realtime PCR. Dilute cDNA to 1/20. Make a master mix containing 10 μl 2× buffer (2× buffer:ABsolute QPCR SYBR Green Rox Mix, Thermo Scientific), 6.6 μl H₂O, and 1.4 μl primers (1 uM mix—forward primer 5'-TAATACGACTCACTATAGG-GAGAGAAACTGAAACACTGGGAC-3' (SEQ ID NO:6), reverse primer 5'-GGAGAACCAATTGCATCTCTAC-3' (SEQ ID NO:7)) and mix with 2 μl diluted cDNA. PCR conditions as follows: (a) 50° C. for 2 minutes; (b) 95° C. for 15 minutes; (c) 95° C. for 15 seconds; (d) 60° C. for 30 seconds; (e) 70° C. for 31 seconds (reading plate); (f) repeat steps (c)-(e) 40 times; (g) 72° C. for 2 minutes. Additionally, include a melting curve step.

Figure 2:
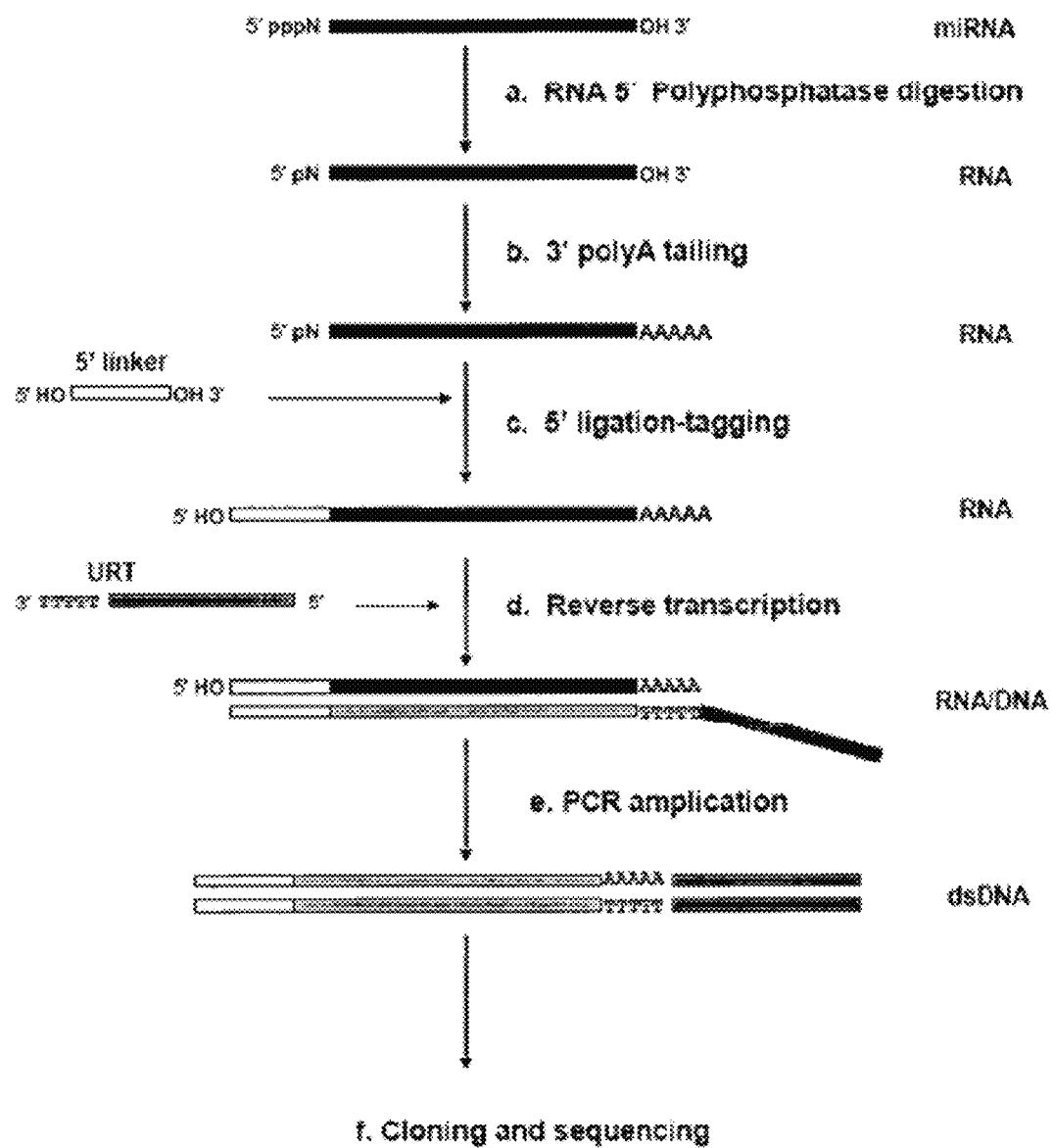
FIG. 2. microRNA identification by PCR or cloning. a. RNA 5' polyphosphatase digestion—use RNA 5' polyphosphatase to remove the γ and β phosphates from microRNAs for use in 5'-T4 RNA ligase-mediated RNA tagging strategies. b. 3'polyA tailing—add polyA at the 3' end of microRNAs for reverse transcription. c. 5' ligation-tagging—use T4 RNA ligase to ligate ss RNA linker to the 5' end of microRNAs. d. Reverse transcription—use URT (U.S. Pat. No. 7,141,372) containing oligo $(dT)_{21}$ and a 3' anchor to synthesize cDNA. Because 5' and 3' sequences of cDNA is known, cDNA can be amplified with PCR. e. PCR amplification—use the minimum cycle number to amplify cDNA in order to get linear amplification. f. Cloning and sequencing—use conventional methods to clone PCR products into the plasmids and sequence them.
Figure 3A:
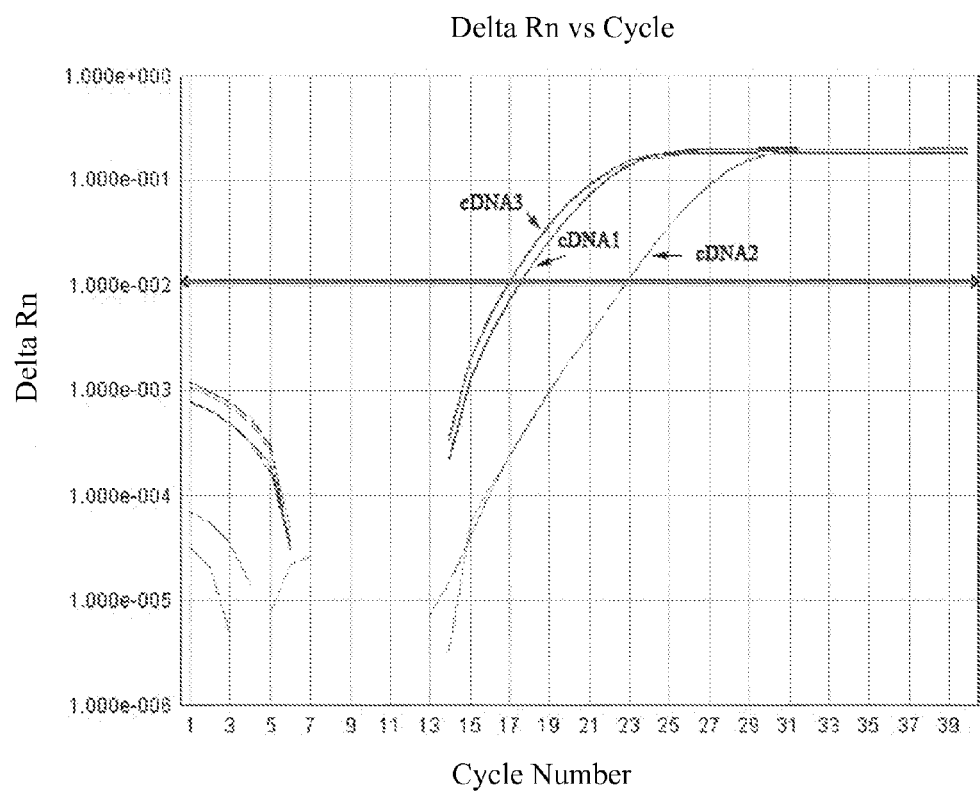
FIG. 3A-3B. Amplification plot and dissociation of miR-200c from a portion of the TCF8-3'UTR. (A) Delta Ct (original (cDNA1)-unbound (cDNA2)) is −5.22. It means that only 2.68% of the miR-200c remains unbound to the bead immobilized 3'-UTR after hybridization. At the same time, 97.32% of the miR-200c is bound to the beads, including specifically and non-specifically bound miR-200c. Delta Ct (original (cDNA1)-released (cDNA3)) is 0.6. It means that the previously 3'-UTR-bound, released miR-200c (cDNA3) is 151.57 percent of the original miR-200c (cDNA1). In principle, the released rate (151.57%) should not be larger than 97.32%. This discrepancy is caused by experimental error, as per replicate experiments (not shown). In short, almost all the miR-200c is recovered, and therefore bound to the TCF8-3'-UTR fragment used as bait. (B) The unique peak of the dissociation curve shows that there are only specific PCR products.
Figure 3B:
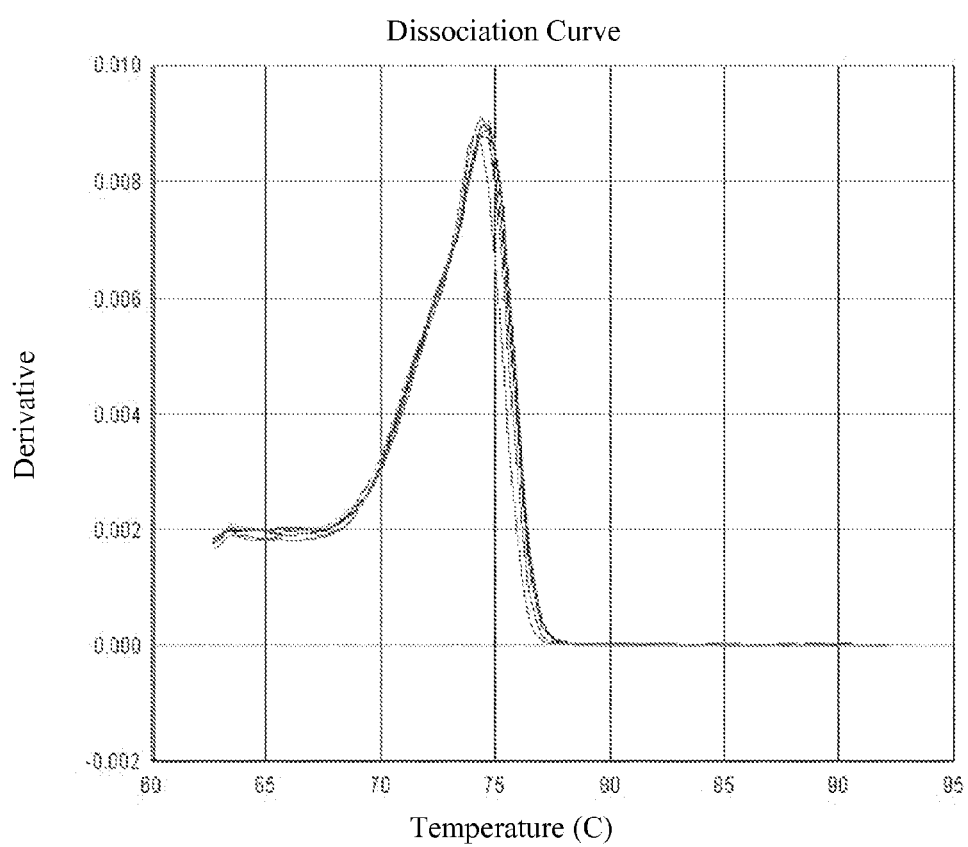
Figure 4A:
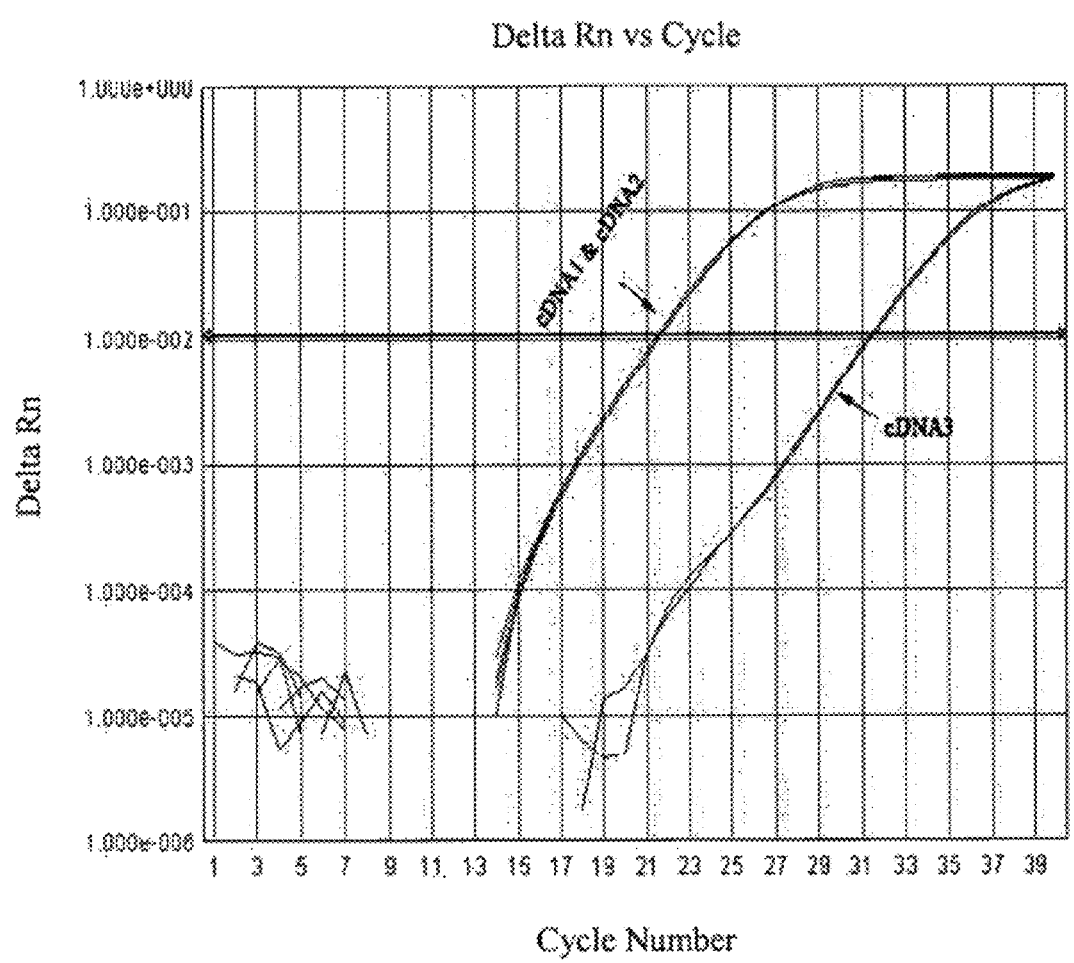
FIG. 4A-4B. Amplification plot and dissociation of miR-20a. (A) Delta Ct (original (cDNA1)-unbound (cDNA2)) is −0.16. It means that there is 89.5% miR-20a unbound to the beads after hybridization. At the same time, there is only 10.5% miR-20a bound to the beads. Delta Ct (original (cDNA1)-released (cDNA3)) is −9.98. It means that the released miR-20a (cDNA3) is 0.1 percent of the original miR-20a (cDNA1). In short, the previously 3'-UTR-bound and released miR-20a is a very small proportion of the original miR-20a. (B) The unique peak of the dissociation curve shows that there are only specific PCR products.
Figure 4B:
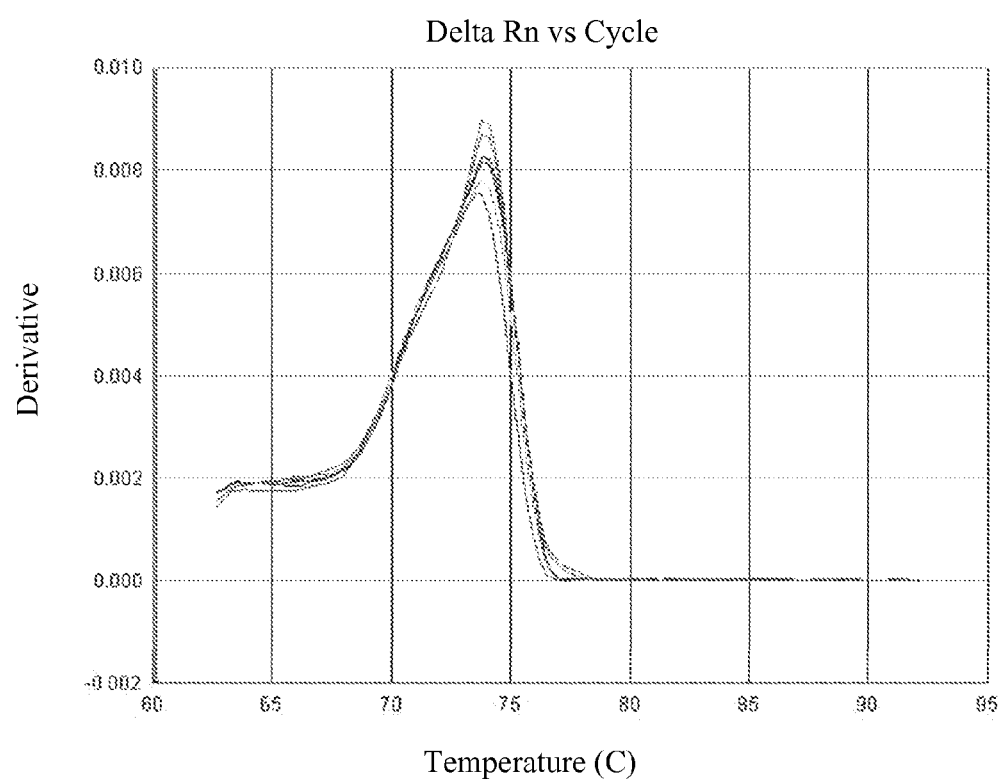
Figure 5A:
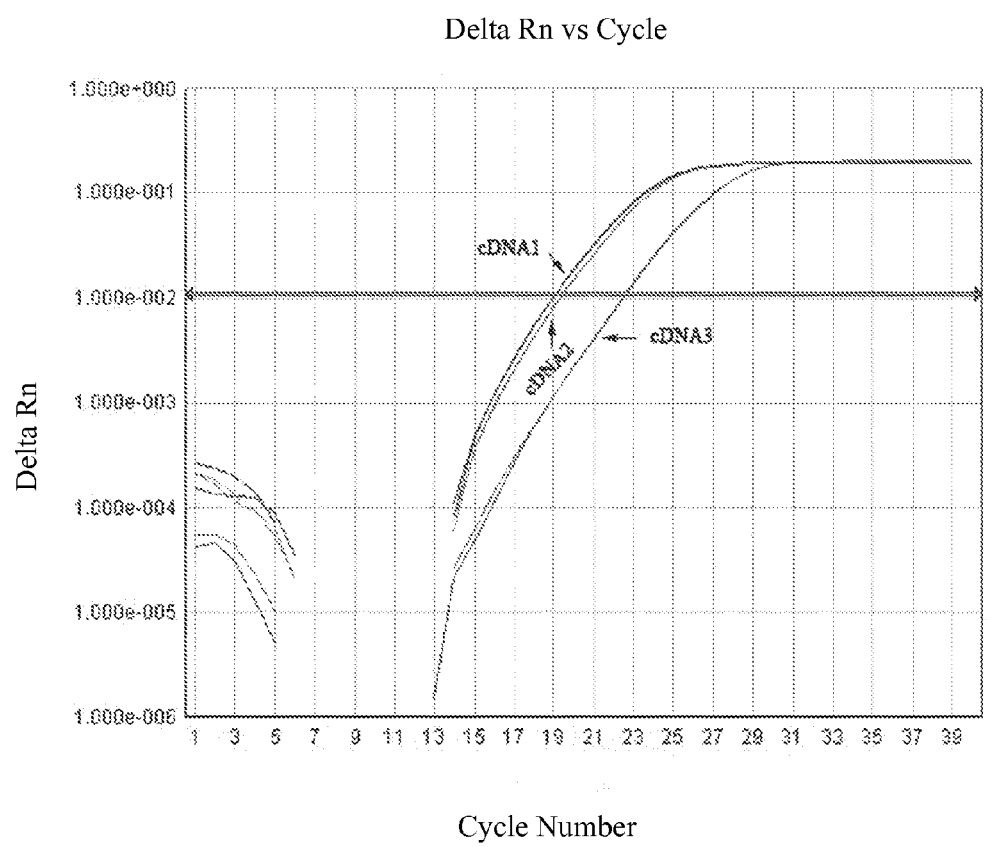
FIG. 5A-5B. Amplification plot and dissociation of miR-34a. (A) Delta Ct (original (cDNA1)-unbound (cDNA2)) is −0.43. It means that there is 74.23% miR-34a unbound to the beads after hybridization. At the same time, there is only 25.77% miR-34a bound on the beads. Delta Ct (original (cDNA1)-released (cDNA3)) is −3.51. It means that the released miR-34a is 8.78 percent of the original miR-34a. In short, the previously 3'-UTR-bound, released miR-34a is a very small proportion of the original miR-34a. (B) The unique peak of the dissociation curve shows that there are only specific PCR products.
Figure 5B:
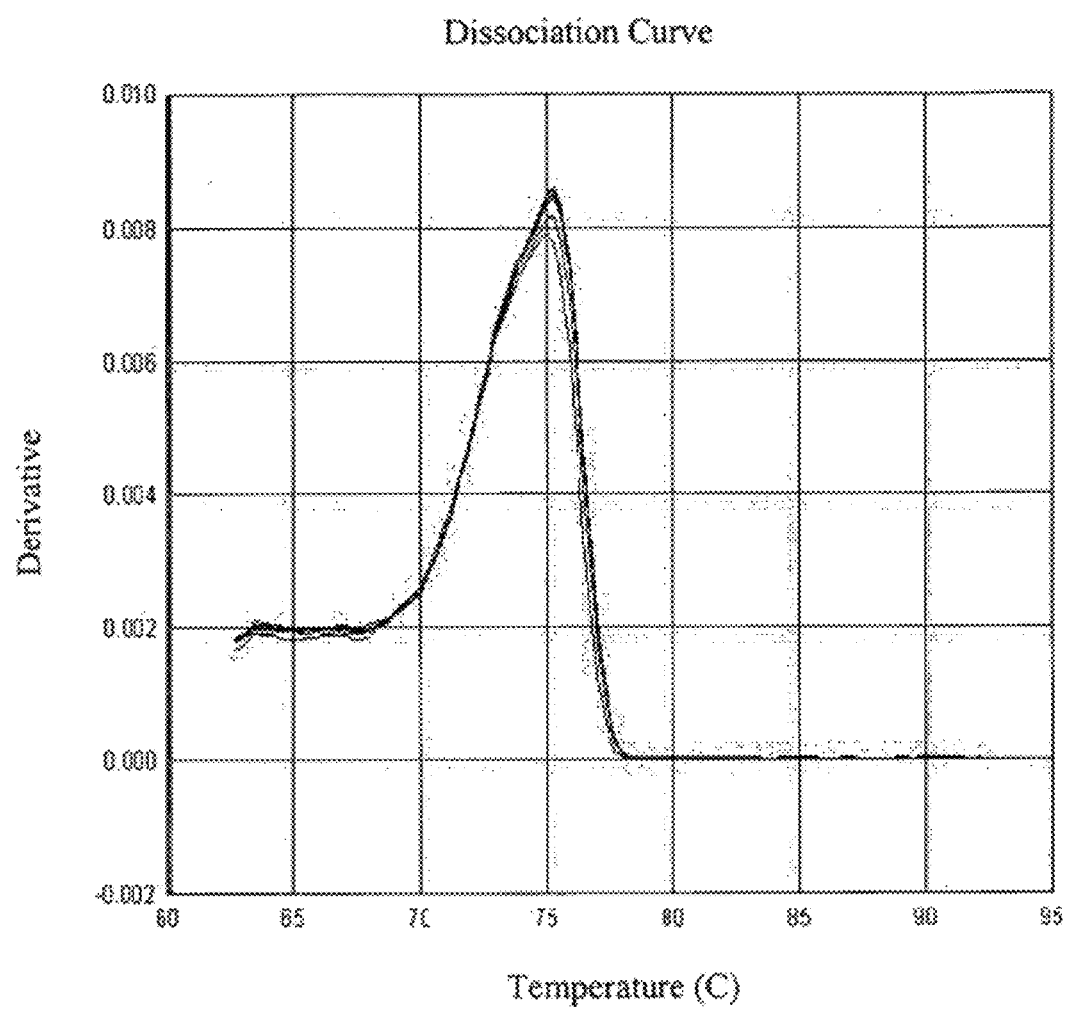
Figure 6A:
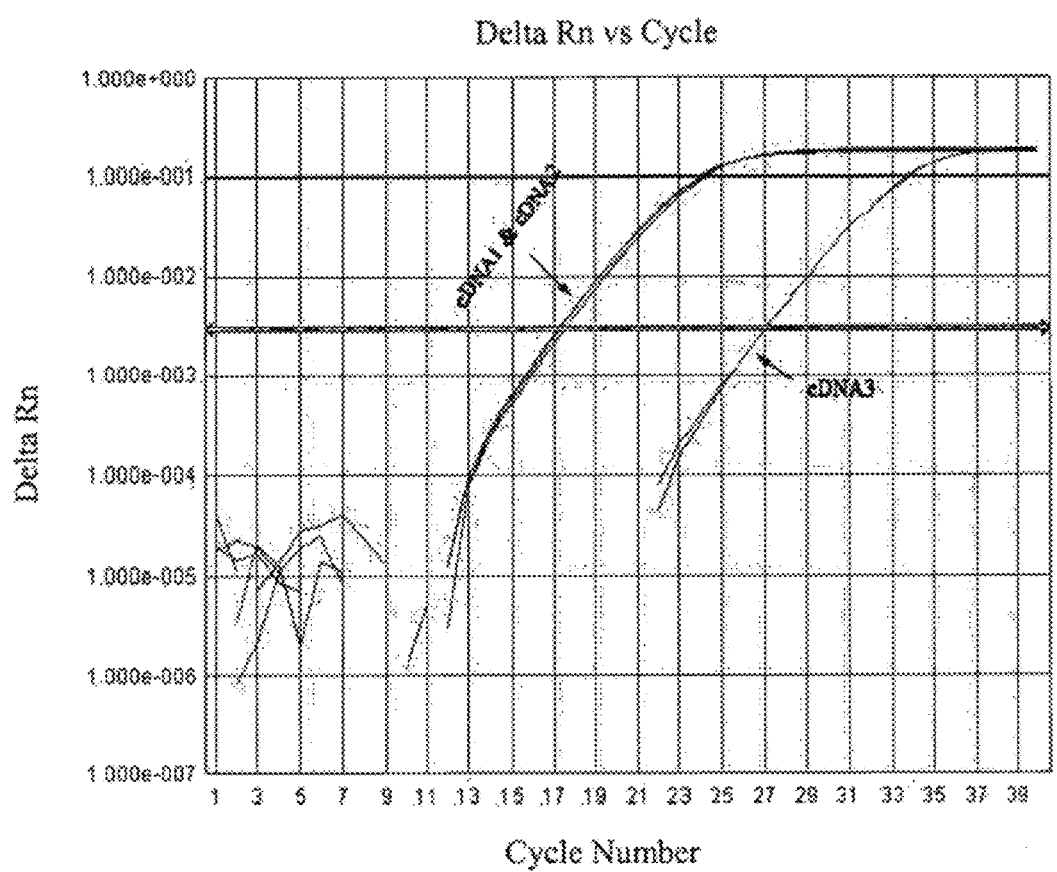
FIG. 6A-6B. Amplification plot and dissociation of miR-100. (A) Delta Ct (original (cDNA1)-unbound (cDNA2)) is −0.24. It means that there is 84.54% miR-100 unbound to the beads after hybridization. At the same time, there is only 15.46% miR-100 bound to the beads. Delta Ct (original (cDNA1)-released (cDNA3)) is −9.85. It means that the released miR-34a is 0.11 percent of the original miR-100. In short, the previously 3'-UTR-bound, released miR-34a is a very small proportion of the original miR-100. (B) The unique peak of the dissociation curve shows that there are only specific PCR products.
Figure 6B:
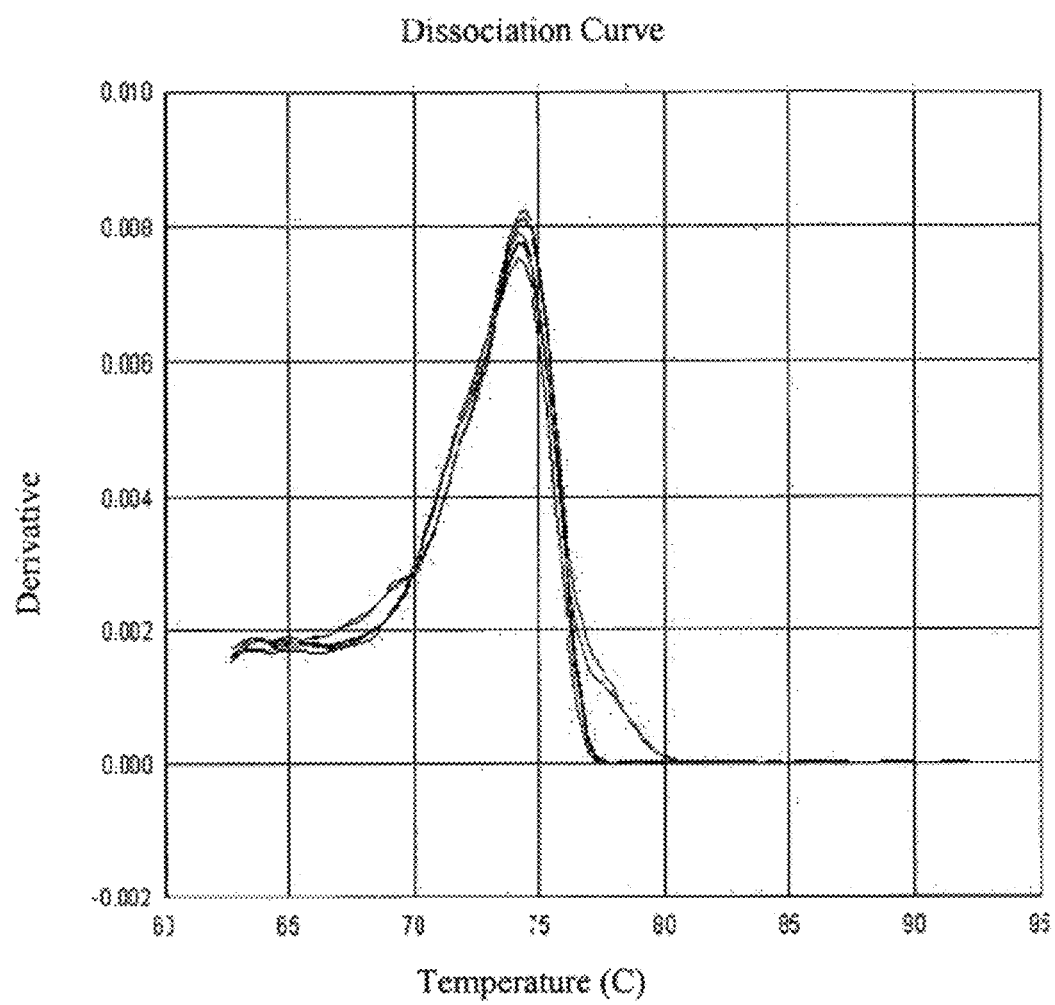
Figure 7A:
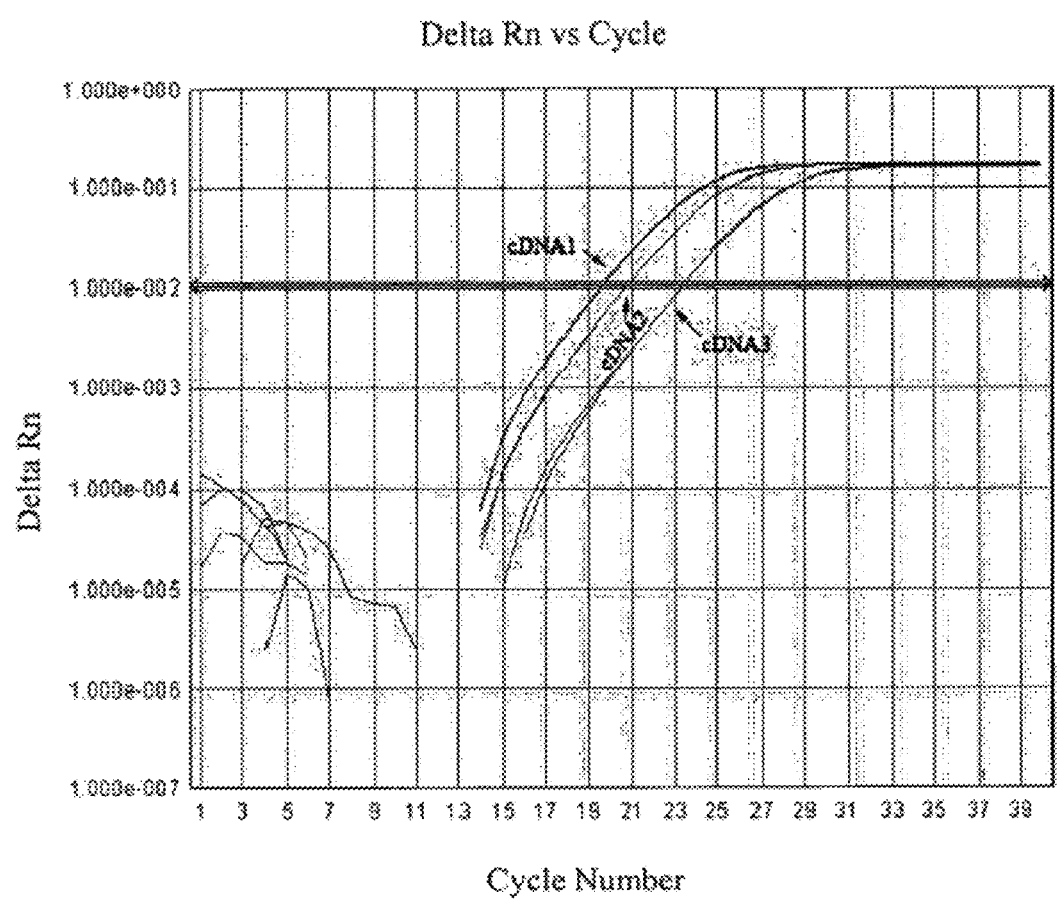
FIG. 7A-7B. Amplification plot and dissociation of miR-150. (A) Delta Ct (original (cDNA1)-unbound (cDNA2)) is −1.13. It means that there is 45.69% miR-150 unbound to the beads after hybridization. At the same time, there is 54.31% miR-150 bound to the beads. Delta Ct (original (cDNA1)-released (cDNA3)) is −3.77. It means that the released miR-150 is 7.33 percent of the original miR-150. In short, the previously 3'-UTR-bound and released miR-150 is a small but measureable proportion of the original miR-150. (B) The unique peak of the dissociation curve shows that there are only specific PCR products.
Figure 7B:
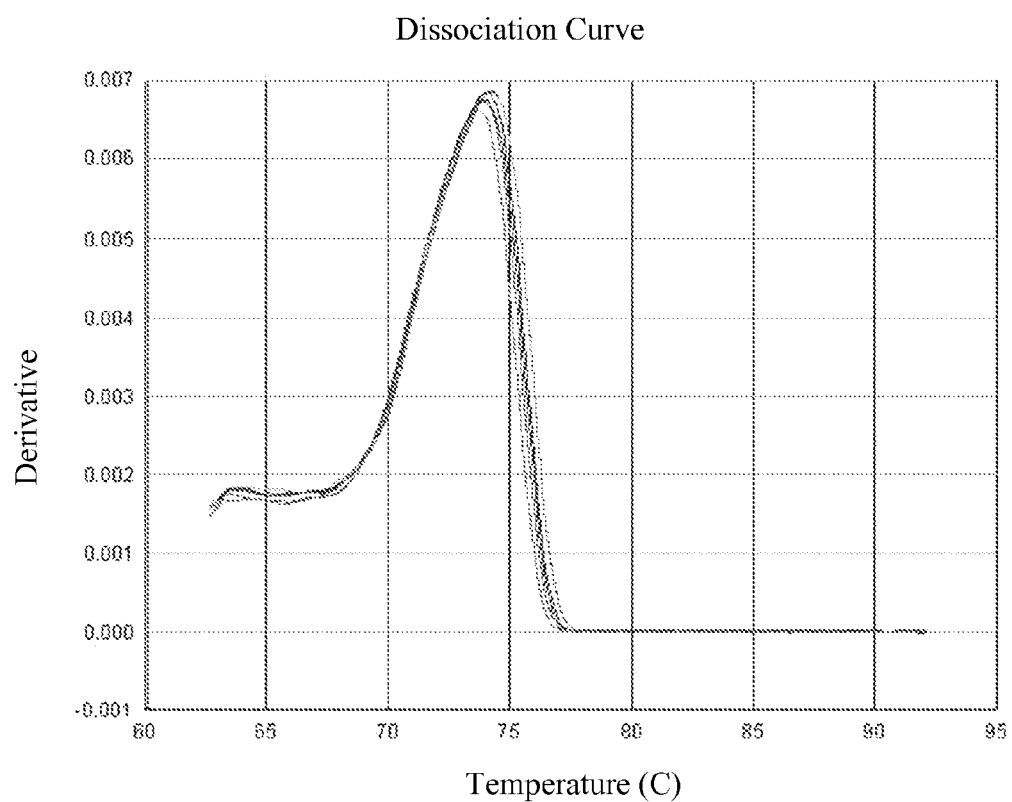

Results from TCF-8 pull-down are shown in FIGS. 1-7. Summary results from partial fragment TCF8-3'UTR trap/bait for pull-down of a synthetic microRNA mixture are shown in Table 1. From the table, 200c is completely bound (>100% implies pipetting error). Although the bound rate of miR-150 (54.31%) is slightly larger than that of miR-34a (25.77%), the released rate of miR-150 (7.33%) is equivalent to that of miR-34a (8.78%). In principle, the higher the bound rate, the higher release rate. It can be concluded that almost all miR-200c is bound to TCF8-3"UTR and therefore released/recovered, while a much smaller proportions of other microRNAs are bound, and therefore recovered.

TABLE 1

|  | 200c | 20a | 34a | 100 | 150 |
| --- | --- | --- | --- | --- | --- |
| Delta Ct(original-unbound) | −5.22 | −0.16 | −0.43 | −0.24 | −1.13 |
| unbound rate | 2.68% | 89.50% | 74.23% | 84.54% | 45.69% |
| Delta Ct(original-released) | 0.60 | −9.98 | −3.51 | −9.85 | −3.77 |
| released rate | 151.57% | 0.10% | 8.78% | 0.11% | 7.33% |

To directly verify, the previously TCF-8 3'-UTR-bound microRNAs, originating from the same synthetic microRNA pool, the released microRNAs were then cloned and sequenced. Results of cloning and sequencing those elements released from the TCF 8 3'UTR trap yielded 18 sequences. Ten sequences are from miR-200c and seven sequences are from miR-200b. The other one sequence is from in vitro transcription DNA template of miR-150 and contains part of T7 promoter sequence and miR-150. The result shows this assay is very specific and efficient for detection of specific microRNAs bound to a given target mRNA.

Cloning/sequences results (sequence and identity) are as follows:

| Sequence | ID | Group |
|---|---|---|
| GGGTAATACTGCCGGGTAATGATGGAT | (SEQ ID NO: 8) | |
| GGGGGTAATACTGCCGGGTAATGATGG | (SEQ ID NO: 9) | |
| GGGTAATACTGCCGGGTAATGATGGATC | (SEQ ID NO: 10) | |
| GGGTAATACTGCCGGGTAATGATGGAT | (SEQ ID NO: 8) | |
| GGTAATACTGCCGGGTAATGATGAC | (SEQ ID NO: 11) | miR-200C |
| GGGTAATACTGCCGGGTAATGATGGAT | (SEQ ID NO: 8) | |
| GGGTAATACTGCCGGGTAATGATGGAT | (SEQ ID NO: 8) | |
| GGGGTAATACTGCCGGGTAATGATGGG | (SEQ ID NO: 12) | |
| GGGTAATACTGCCGGGTAGTGATGGATC | (SEQ ID NO: 13) | |
| GGGGTAATACTGCCGGGTAATGAT | (SEQ ID NO: 14) | |
| GGTAATACTGCCTGGTAATGATG | (SEQ ID NO: 15) | |
| GGTAATACTGCCTGGTAATGATGAAC | (SEQ ID NO: 16) | |
| GCTAATACTGCCTGGTAATGATC | (SEQ ID NO: 17) | |
| GGTAATACTGCCTGGTAATGATG | (SEQ ID NO: 15) | miR-200b |
| GGTAATACTGCCTGGTAATGAT | (SEQ ID NO: 18) | |
| GGTAATACTGCCTGGTAATGATG | (SEQ ID NO: 15) | |
| GGTAACACTGCCTGGTAATGATGAC | (SEQ ID NO: 19) | |
| ACTCACTATAGGTCTCCCAAC | (SEQ ID NO: 20) | DNA template of miR-150 |

Example 2

Isolate Specific microRNAs to Target the Partial 3'UTR of TCF8 from Entire Pool of miRNAs Derived from NHBE Cells The pool of hundreds of miRNAs inherent to cells are clearly a more complex matrix than a synthesized microRNA pool of 10-15 microRNAs. This is verification of a complex mixed nucleic acid system.

The same protocol is used as in Example 1 with the unique feature of this example being that miRNAs are from NHBE cells (and not from a synthesized miRNA pool). After microRNA pull-down, perform realtime PCR to check quantities of some microRNAs and cloning to check the varieties of the released microRNA.

Realtime PCR results for all cellular pooled microRNA pull-down, using partial TCF8 3'UTR (502 bp fragment), are shown in Table 2. Positive control 200c released rate is high, at about 89%.

TABLE 2

|  | 200c | 20a | 22 | 205 | 221 | 320a |
|---|---|---|---|---|---|---|
| Delta Ct (original-unbound) | −6.43 | −1.01 | −9.93 | −2.93 | −3.66 | −4.03 |

TABLE 2-continued

|  | 200c | 20a | 22 | 205 | 221 | 320a |
|---|---|---|---|---|---|---|
| unbound rate | 1.16% | 49.65% | 0.10% | 13.12% | 7.91% | 6.12% |
| Delta Ct (original-released) | −0.17 | −7.81 | −3.05 | −6.21 | −2.45 | −1.1 |
| released rate | 88.88% | 0.45% | 12.07% | 1.35% | 18.30% | 46.65% |

Cloning/sequences results (sequence and identity) are as follows:

| Sequence | ID | Group |
|---|---|---|
| TAATACTGCCGGGTAATGATGGTT | (SEQ ID NO: 21) | miR-200c |
| TAATACTGCCGGGTAATGATGG | (SEQ ID NO: 22) | |
| AGCTACATTGTCTGCTGGGTTTCT | (SEQ ID NO: 23) | |
| AGCTACATTGTCTGCTGGGTTTCT | (SEQ ID NO: 23) | |
| AGCTACATTGTCTGCTGGGTTTC | (SEQ ID NO: 24) | miR-221 |
| AGCTACATTGTCTGCTGGGTTTC | (SEQ ID NO: 24) | |
| AGCTACATTGTCTGCTGGGTTTC | (SEQ ID NO: 24) | |
| AAAAGCTGGGTTGAGAGGGCG | (SEQ ID NO: 25) | |
| AAAAGCTGGGTTGAGAGGGCG | (SEQ ID NO: 25) | miR-320 |
| AAAAGCTGGGTTGAGAGGGCG | (SEQ ID NO: 25) | |
| AAAAGCTGGGTTGAGAGGGC | (SEQ ID NO: 26) | |
| AAGCTGCCAGTTGAAGAACTGTT | (SEQ ID NO: 27) | miR-22 |
| AAGCTGCCAGTTGAAGAACTGT | (SEQ ID NO: 28) | |
| TCCTTCATTCCACCGGAGTCTG | (SEQ ID NO: 29) | miR-205 |
| TCCTTCATTCCACCGGAGTCT | (SEQ ID NO: 30) | |

```
GGGAGAATTAGCTGAGGCCTGGCCCT                      (SEQ ID NO: 31)    no ID matches GCTAAACCTAGCCCCAAACCCACTCCACCTTACTACCAGACAACCAAAAAAG  (SEQ ID NO: 32)    no matches GCTAAACCTAGCCCCAAACCCACTCCACCTT                 (SEQ ID NO: 33)    no ID matches GTTACACCCTAGTAGGCTCCCTTCCCCTACTC                (SEQ ID NO: 34)    no ID matches GATGTGTCCCTAGCCATCTTAATGCCCTCATCCCCTC           (SEQ ID NO: 35)    no ID matches
```

For sequencing, 2 copies of positive control 200c in 20 colonies, and also several other microRNAs, such as miR-221, 320a, 22, 205 were detected.

Example 3

Isolate Specific microRNAs to Target the Full Length 3'UTR of TCF8 from miRNAs of NHBE Cells The full 3'UTR of TCF8 is 1932 nt and the partial 3'UTR of TCF8 (used in Examples 1 and 2 above) is only 502 nt. This full length UTR-release assay is verification of performance in a more complex mixed nucleic acid system Except the forward and reverse primers, the same protocol is used as in Example 2, with the unique feature of this example being that miRNAs are pulled down using a full length 3'UTR, as well as deriving from NHBE cells (and not from a synthesized miRNA pool of <20 microRNAs). After microRNA pull-down, realtime PCR was performed to check quantities of several microRNAs, bound and free, and cloning was performed to check the varieties of the released microRNA. During microRNA pull-down: (1) the forward primer for PCR amplification of full TCF8-3'UTR was 5' TAATACGACTCACTATAGGGAGACAAAT-GAAGCCTAATCGT-3' (SEQ ID NO: 36); (2) the reverse primer is 5'-CATTTTATTGTGAGATGGGAGTC-3' (SEQ ID NO: 37).

Realtime PCR results are shown in Table 3. Positive control 200c released rate is very high at about 100% (118.9%, inclusive of likely pipetting error)

TABLE 3

|  | 200c | 20a | 22 | 205 | 221 | 320a |
|---|---|---|---|---|---|---|
| Delta Ct (original-unbound) | −6.17 | −0.66 | −3.12 | −0.72 | −0.97 | −2.26 |
| unbound rate | 1.39% | 63.29% | 11.50% | 60.71% | 51.05% | 20.88% |
| Delta Ct (original-released) | 0.25 | −4.24 | −2.14 | −5.08 | −5.4 | −2.38 |
| released rate | 118.92% | 5.29% | 22.69% | 2.96% | 2.37% | 19.21% |

Cloning/sequences results (sequence and identity) are as follows:

```
TAATACTGCCTGGTAATGATGACT    (SEQ ID NO: 38)  ⎫
TAATACTGCCTGGTAATGATGACT    (SEQ ID NO: 38)  ⎬  miR-200b + miR-200C
TAATACTGCCGGGTAATGATGG      (SEQ ID NO: 39)  ⎭

CAAAGTGCTTACAGTGCAGGT       (SEQ ID NO: 40)  ⎫
CAAAGTGCTTACAGTGCAGGT       (SEQ ID NO: 40)  ⎬  miR-17
CAAAGTGCTTACAGTGCAGGTAG     (SEQ ID NO: 41)  ⎪
CAAAGTGCTTACAGTGCAGGT       (SEQ ID NO: 40)  ⎭

GAGATGGGAGTCTGG             (SEQ ID NO: 42)  ⎫
GAGATGGGAGTCTGG             (SEQ ID NO: 42)  ⎬  no ID matches
GAGATGGGAGTCTG              (SEQ ID NO: 43)  ⎪
GATGGGAGTCTG                (SEQ ID NO: 44)  ⎭

AAAAGCTGGGTTGAGAGGGCGGC     (SEQ ID NO: 45)  ⎫  miR-320a
AAAAGCTGGGTTGAGAGGGCG       (SEQ ID NO: 46)  ⎭

TCCTTCATTCCACCGGAGTCTG      (SEQ ID NO: 47)     miR-205

AAGCTGCCAGTTGAAGAACTGT      (SEQ ID NO: 48)     miR-22

AGCTACATTGTCTGCTGGGTTTC     (SEQ ID NO: 49)     miR-221

TGAGGTAGTAGGTTGTGTGGTT      (SEQ ID NO: 50)     let-7b

TGCGGGGCTAGGGCTAACAG        (SEQ ID NO: 51)     miR-744

AAGCTCAAGAATAACGAAAACGGAC   (SEQ ID NO: 52)     no ID matches

GGTAGCGTGGCCGAGCGG          (SEQ ID NO: 53)     no ID matches

GAAGCGGGTGCTCTTATTTT        (SEQ ID NO: 54)     no ID matches
```

For sequencing, three copies of positive control 200b and 200c were detected in 20 colonies. Therefore, other unpredicted microRNAs were discovered as binding TCF-8, such as miR-17, 320a, 221, 22, 205.

Using the TCF-8 3'UTR (known target and microRNAs), miR-200c, miR-20a, miR-34a, and miR-100 were amplified from the target-released material by RNA-specific realtime qRT-PCR. It can be seen (Example 2, Table 2) that the released rate (88.88%) of miR-200c is still very high in this complex system (encompassing the entire cellular pool of microRNAs). For miR-20a, miR-34a, and miR-100, the result is clear (no binding) in the complicated system than in the simple system (encompassing only the microRNA pool).

Examples 2 and 3 show the released rates of positive control 200c are very high (88.88% and 118.92%, resp.) in both whole cell miRNA pulldown with partial TCF8_3'UTR and whole cell miRNA pulldown with full length TCF8_3'UTR. Furthmore, positive control 200b and 200c were always found in cloned sequences. The qPCR and cloning results demonstrate that the microRNA binding assay invention can work in complex relevant cell-derived systems.

What is claimed is:

1. A method for determining which microRNAs bind to a target mRNA comprising the steps of
   (a) creating a 3'UTR_RNA from the target mRNA by creating a double-stranded 3'UTR from the target mRNA by reverse transcription of the mRNA to synthesize cDNA and polymerase chain reaction (PCR) of the cDNA; and synthesizing 3'UTR_RNA from the double stranded 3'UTR PCR product using in vitro transcription;
   (b) creating a bait sequence from the target mRNA, where the bait sequence comprises a biotinylated cRNA of a 3' untranslated region (UTR) that binds to a binding agent and where the bait sequence comprises the 3'UTR_RNA;
   (c) adding a mixture of microRNAs to the bait sequence;
   (d) separating the microRNAs that bind to the bait sequence from those microRNAs that do not bind; and
   (e) identifying the microRNAs that bind to the bait sequence, wherein the microRNAs identified are those that bind to the target mRNA.

2. The method of claim 1, further comprising the step of releasing the bound microRNAs from the bait sequence before identifying the microRNAs.

3. The method of claim 1, further comprising immobilizing the bait sequence to a substrate before adding the microRNAs.

4. The method of claim 3, wherein the bait sequence is immobilized on the substrate by a binding agent.

5. The method of claim 3, wherein the substrate are beads.

6. The method of claim 5, wherein the beads are magnetic.

7. The method of claim 1, wherein the biotinylated cRNA of the 3'UTR is prepared using T7-tagged forward primer SEQ ID NO:6 for partial length of the 3'UTR or SEQ ID NO:45 for full length of the 3'UTR and reverse primer SEQ ID NO: 7 for partial length of the 3'UTR or SEQ ID NO: 46 for full length of the 3'UTR to amplify TCF8 cDNA, and then using T7-based in vitro transcription to integrate biotinylated UTP into the cRNA sequence.

8. The method of claim 6, wherein separating comprises separating the magnetic beads with the microRNAs bound to the bait sequence by introduction of a magnet and removal of the unbound microRNAs.

9. The method of claim 1, wherein separating comprising eluting through a column.

10. The method of claim 1, wherein the transcription is done in the presence of biotin-16-UTP.

11. The method of claim 1, wherein the microRNAs which bind to the target mRNA hybridize with the 3'UTR_RNA.

12. The method of claim 1, wherein the identification of the microRNAs that bind to the bait sequence comprises sequencing.

13. The method of claim 12, wherein sequencing comprises synthesizing cDNA from the microRNAs that bound to the bait sequence and sequencing the cDNA.

14. The method of claim 12, further comprising polyA tailing the 3'end of the microRNAs that bind to the bait sequence, and 5'end ligation tagging of the microRNAs that bind to the bait sequence before sequencing the microRNAs that bind to the bait sequence.

15. The method of claim 12, further comprising 3'end ligation tagging of the microRNAs that bind to the bait sequence, and 5'end ligation tagging of the microRNAs that bind to the bait sequence before sequencing the microRNAs that bind to the bait sequence.

16. The method of claim 14, further comprising the step of reverse transcription of the microRNAs that bind to the bait sequence before sequencing.

17. The method of claim 14, further comprising the step of amplification of the microRNAs that bind to the bait sequence before sequencing.

18. A kit for determining which microRNAs bind to a target mRNA comprising a forward primer having SEQ ID NO:6 or SEQ ID NO:45; biotin;

a 3'-UTR fragment of a mRNA immobilized to a substrate;

reagents for (1) creating a biotinylated 3' untranslated region (UTR)-cRNA bait sequence from the target mRNA; (2) separating the microRNAs that bind to the bait sequence from those microRNAs which do not; and (3) identifying the microRNAs that bind to the bait sequence, wherein the microRNAs identified are those which bind to the target mRNA;

reagents for creating a 3'UTR_RNA bait sequence from the target mRNA by creating double-stranded 3'UTR from the target mRNA; and synthesizing 3'UTR_RNA from the 3'UTR; and instructions for determining which microRNAs bind to a target mRNA comprising the steps of (a) creating a 3'UTR_RNA from the target mRNA by creating a double-stranded 3'UTR from the target mRNA by reverse transcription of the mRNA to synthesize cDNA and polymerase chain reaction (PCR) of the cDNA; and synthesizing 3'UTR_RNA from the double stranded 3'UTR PCR product using in vitro transcription;

(b) creating a bait sequence from the target mRNA, where the bait sequence comprises a biotinylated cRNA of a 3' untranslated region (UTR) that binds to a binding agent and where the bait sequence comprises the 3'UTR_RNA;

(c) adding a mixture of microRNAs to the bait sequence;

(d) separating the microRNAs that bind to the bait sequence from those microRNAs that do not bind; and (e) identifying the microRNAs that bind to the bait sequence, wherein the microRNAs identified are those that bind to the target mRNA.

* * * * *

SEQUENCE LISTING

<160> NUMBER OF SEQ ID NOS: 54

<210> SEQ ID NO 1
<211> LENGTH: 20
<212> TYPE: DNA
<213> ORGANISM: artificial sequence
<220> FEATURE:
<223> OTHER INFORMATION: T7 promoter

<400> SEQUENCE: 1
taatacgact cactataggg                                              20

<210> SEQ ID NO 2
<211> LENGTH: 22
<212> TYPE: DNA
<213> ORGANISM: artificial sequence
<220> FEATURE:
<223> OTHER INFORMATION: M.R.S. miRNA cloning linker, nucleotides at
      positions 7 to 22 have RNA base

<400> SEQUENCE: 2
tggaatucuc gggcaccaag gu                                           22

<210> SEQ ID NO 3
<211> LENGTH: 40
<212> TYPE: DNA
<213> ORGANISM: artificial sequence
<220> FEATURE:
<223> OTHER INFORMATION: URT primer sequence

<400> SEQUENCE: 3
aacgagacga cgacagactt tttttttttt ttttttttv                         40

<210> SEQ ID NO 4
<211> LENGTH: 17
<212> TYPE: DNA
<213> ORGANISM: artificial sequence
<220> FEATURE:
<223> OTHER INFORMATION: primer sequence on 5' linker PCR

<400> SEQUENCE: 4
tggaattctc gggcacc                                                 17

<210> SEQ ID NO 5
<211> LENGTH: 21
<212> TYPE: DNA
<213> ORGANISM: artificial sequence
<220> FEATURE:
<223> OTHER INFORMATION: primer sequence on URT U60

<400> SEQUENCE: 5
aacgagacga cgacagactt t                                            21

<210> SEQ ID NO 6
<211> LENGTH: 42
<212> TYPE: DNA
<213> ORGANISM: artificial sequence
<220> FEATURE:
<223> OTHER INFORMATION: forward primer for PCR amplification of

```
            TCF8_3'UTR

<400> SEQUENCE: 6
taatacgact cactataggg agagaaactg aaacactggg ac                    42

<210> SEQ ID NO 7
<211> LENGTH: 22
<212> TYPE: DNA
<213> ORGANISM: artificial sequence
<220> FEATURE:
<223> OTHER INFORMATION: reverse primer for PCR amplification of
      TCF8_3'UTR

<400> SEQUENCE: 7
ggagaaccaa ttgcatctct ac                                          22

<210> SEQ ID NO 8
<211> LENGTH: 27
<212> TYPE: DNA
<213> ORGANISM: artificial sequence
<220> FEATURE:
<223> OTHER INFORMATION: cDNA of miR-200c element

<400> SEQUENCE: 8
gggtaatact gccgggtaat gatggat                                     27

<210> SEQ ID NO 9
<211> LENGTH: 27
<212> TYPE: DNA
<213> ORGANISM: artificial sequence
<220> FEATURE:
<223> OTHER INFORMATION: cDNA of miR-200c element

<400> SEQUENCE: 9
gggggtaata ctgccgggta atgatgg                                     27

<210> SEQ ID NO 10
<211> LENGTH: 28
<212> TYPE: DNA
<213> ORGANISM: artificial sequence
<220> FEATURE:
<223> OTHER INFORMATION: cDNA of miR-200c element

<400> SEQUENCE: 10
gggtaatact gccgggtaat gatggatc                                    28

<210> SEQ ID NO 11
<211> LENGTH: 25
<212> TYPE: DNA
<213> ORGANISM: artificial sequence
<220> FEATURE:
<223> OTHER INFORMATION: cDNA of miR-200c element

<400> SEQUENCE: 11
ggtaatactg ccgggtaatg atgac                                       25

<210> SEQ ID NO 12
<211> LENGTH: 27
<212> TYPE: DNA
<213> ORGANISM: artificial sequence
<220> FEATURE:
<223> OTHER INFORMATION: cDNA of miR-200c element

<400> SEQUENCE: 12
ggggtaatac tgccgggtaa tgatggg                                     27
```

<210> SEQ ID NO 13
<211> LENGTH: 28
<212> TYPE: DNA
<213> ORGANISM: artificial sequence
<220> FEATURE:
<223> OTHER INFORMATION: cDNA of miR-200c element

<400> SEQUENCE: 13
gggtaatact gccgggtagt gatggatc                      28

<210> SEQ ID NO 14
<211> LENGTH: 24
<212> TYPE: DNA
<213> ORGANISM: artificial sequence
<220> FEATURE:
<223> OTHER INFORMATION: cDNA of miR-200c element

<400> SEQUENCE: 14
ggggtaatac tgccgggtaa tgat                          24

<210> SEQ ID NO 15
<211> LENGTH: 23
<212> TYPE: DNA
<213> ORGANISM: artificial sequence
<220> FEATURE:
<223> OTHER INFORMATION: cDNA of miR-200b element

<400> SEQUENCE: 15
ggtaatactg cctggtaatg atg                           23

<210> SEQ ID NO 16
<211> LENGTH: 26
<212> TYPE: DNA
<213> ORGANISM: artificial sequence
<220> FEATURE:
<223> OTHER INFORMATION: cDNA of miR-200b element

<400> SEQUENCE: 16
ggtaatactg cctggtaatg atgaac                        26

<210> SEQ ID NO 17
<211> LENGTH: 23
<212> TYPE: DNA
<213> ORGANISM: artificial sequence
<220> FEATURE:
<223> OTHER INFORMATION: cDNA of miR-200b element

<400> SEQUENCE: 17
gctaatactg cctggtaatg atc                           23

<210> SEQ ID NO 18
<211> LENGTH: 22
<212> TYPE: DNA
<213> ORGANISM: artificial sequence
<220> FEATURE:
<223> OTHER INFORMATION: cDNA of miR-200b element

<400> SEQUENCE: 18
ggtaatactg cctggtaatg at                            22

<210> SEQ ID NO 19
<211> LENGTH: 25
<212> TYPE: DNA
<213> ORGANISM: artificial sequence
<220> FEATURE:
<223> OTHER INFORMATION: cDNA of miR-200b element

```
<400> SEQUENCE: 19
ggtaacactg cctggtaatg atgac                                          25

<210> SEQ ID NO 20
<211> LENGTH: 21
<212> TYPE: DNA
<213> ORGANISM: artificial sequence
<220> FEATURE:
<223> OTHER INFORMATION: DNA template of miR-150

<400> SEQUENCE: 20
actcactata ggtctcccaa c                                              21

<210> SEQ ID NO 21
<211> LENGTH: 24
<212> TYPE: DNA
<213> ORGANISM: artificial sequence
<220> FEATURE:
<223> OTHER INFORMATION: cDNA of miR-200c element

<400> SEQUENCE: 21
taatactgcc gggtaatgat ggtt                                           24

<210> SEQ ID NO 22
<211> LENGTH: 22
<212> TYPE: DNA
<213> ORGANISM: artificial sequence
<220> FEATURE:
<223> OTHER INFORMATION: cDNA of miR-200c element

<400> SEQUENCE: 22
taatactgcc gggtaatgat gg                                             22

<210> SEQ ID NO 23
<211> LENGTH: 24
<212> TYPE: DNA
<213> ORGANISM: artificial sequence
<220> FEATURE:
<223> OTHER INFORMATION: cDNA of miR-221 element

<400> SEQUENCE: 23
agctacattg tctgctgggt ttct                                           24

<210> SEQ ID NO 24
<211> LENGTH: 23
<212> TYPE: DNA
<213> ORGANISM: artificial sequence
<220> FEATURE:
<223> OTHER INFORMATION: cDNA of miR-221 element

<400> SEQUENCE: 24
agctacattg tctgctgggt ttc                                            23

<210> SEQ ID NO 25
<211> LENGTH: 21
<212> TYPE: DNA
<213> ORGANISM: artificial sequence
<220> FEATURE:
<223> OTHER INFORMATION: cDNA of miR-320 element

<400> SEQUENCE: 25
aaaagctggg ttgagagggc g                                              21

<210> SEQ ID NO 26
```

```
<211> LENGTH: 20
<212> TYPE: DNA
<213> ORGANISM: artificial sequence
<220> FEATURE:
<223> OTHER INFORMATION: cDNA of miR-320 element

<400> SEQUENCE: 26
aaaagctggg ttgagagggc                                                    20

<210> SEQ ID NO 27
<211> LENGTH: 23
<212> TYPE: DNA
<213> ORGANISM: artificial sequence
<220> FEATURE:
<223> OTHER INFORMATION: cDNA of miR-22 element

<400> SEQUENCE: 27
aagctgccag ttgaagaact gtt                                                23

<210> SEQ ID NO 28
<211> LENGTH: 22
<212> TYPE: DNA
<213> ORGANISM: artificial sequence
<220> FEATURE:
<223> OTHER INFORMATION: cDNA of miR-22 element

<400> SEQUENCE: 28
aagctgccag ttgaagaact gt                                                 22

<210> SEQ ID NO 29
<211> LENGTH: 22
<212> TYPE: DNA
<213> ORGANISM: artificial sequence
<220> FEATURE:
<223> OTHER INFORMATION: cDNA of miR-205 element

<400> SEQUENCE: 29
tccttcattc caccggagtc tg                                                 22

<210> SEQ ID NO 30
<211> LENGTH: 21
<212> TYPE: DNA
<213> ORGANISM: artificial sequence
<220> FEATURE:
<223> OTHER INFORMATION: cDNA of miR-205 element

<400> SEQUENCE: 30
tccttcattc caccggagtc t                                                  21

<210> SEQ ID NO 31
<211> LENGTH: 26
<212> TYPE: DNA
<213> ORGANISM: artificial sequence
<220> FEATURE:
<223> OTHER INFORMATION: cDNA of unknown element

<400> SEQUENCE: 31
gggagaatta gctgaggcct ggccct                                             26

<210> SEQ ID NO 32
<211> LENGTH: 52
<212> TYPE: DNA
<213> ORGANISM: artificial sequence
<220> FEATURE:
<223> OTHER INFORMATION: cDNA of unknown element

<400> SEQUENCE: 32
```
gctaaaccta gccccaaacc cactccacct tactaccaga caaccaaaaa ag    52

<210> SEQ ID NO 33
<211> LENGTH: 31
<212> TYPE: DNA
<213> ORGANISM: artificial sequence
<220> FEATURE:
<223> OTHER INFORMATION: cDNA of unknown element

<400> SEQUENCE: 33
gctaaaccta gccccaaacc cactccacct t    31

<210> SEQ ID NO 34
<211> LENGTH: 32
<212> TYPE: DNA
<213> ORGANISM: artificial sequence
<220> FEATURE:
<223> OTHER INFORMATION: cDNA of unknown element

<400> SEQUENCE: 34
gttacaccct agtaggctcc cttcccctac tc    32

<210> SEQ ID NO 35
<211> LENGTH: 37
<212> TYPE: DNA
<213> ORGANISM: artificial sequence
<220> FEATURE:
<223> OTHER INFORMATION: cDNA of unknown element

<400> SEQUENCE: 35
gatgtgtccc tagccatctt aatgccctca tcccctc    37

<210> SEQ ID NO 36
<211> LENGTH: 41
<212> TYPE: DNA
<213> ORGANISM: artificial sequence
<220> FEATURE:
<223> OTHER INFORMATION: forward primer for PCR amplication of full
    TCF8-3'UTR

<400> SEQUENCE: 36
taatacgact cactataggg agacaaatga agcctaatcg t    41

<210> SEQ ID NO 37
<211> LENGTH: 23
<212> TYPE: DNA
<213> ORGANISM: artificial sequence
<220> FEATURE:
<223> OTHER INFORMATION: reverse primer for PCR amplification of full
    TCF8-3'UTR

<400> SEQUENCE: 37
cattttattg tgagatggga gtc    23

<210> SEQ ID NO 38
<211> LENGTH: 24
<212> TYPE: DNA
<213> ORGANISM: artificial sequence
<220> FEATURE:
<223> OTHER INFORMATION: cDNA of miR-200b+miR-200c element

<400> SEQUENCE: 38
taatactgcc tggtaatgat gact    24

<210> SEQ ID NO 39

```
<211> LENGTH: 22
<212> TYPE: DNA
<213> ORGANISM: artificial sequence
<220> FEATURE:
<223> OTHER INFORMATION: cDNA of miR-200b+miR-200c element

<400> SEQUENCE: 39
taatactgcc gggtaatgat gg                                            22

<210> SEQ ID NO 40
<211> LENGTH: 21
<212> TYPE: DNA
<213> ORGANISM: artificial sequence
<220> FEATURE:
<223> OTHER INFORMATION: cDNA of miR-17 element

<400> SEQUENCE: 40
caaagtgctt acagtgcagg t                                             21

<210> SEQ ID NO 41
<211> LENGTH: 23
<212> TYPE: DNA
<213> ORGANISM: artificial sequence
<220> FEATURE:
<223> OTHER INFORMATION: cDNA of miR-17 element

<400> SEQUENCE: 41
caaagtgctt acagtgcagg tag                                           23

<210> SEQ ID NO 42
<211> LENGTH: 15
<212> TYPE: DNA
<213> ORGANISM: artificial sequence
<220> FEATURE:
<223> OTHER INFORMATION: cDNA of unknown element

<400> SEQUENCE: 42
gagatgggag tctgg                                                    15

<210> SEQ ID NO 43
<211> LENGTH: 14
<212> TYPE: DNA
<213> ORGANISM: artificial sequence
<220> FEATURE:
<223> OTHER INFORMATION: cDNA of unknown element

<400> SEQUENCE: 43
gagatgggag tctg                                                     14

<210> SEQ ID NO 44
<211> LENGTH: 12
<212> TYPE: DNA
<213> ORGANISM: artificial sequence
<220> FEATURE:
<223> OTHER INFORMATION: cDNA of unknown element

<400> SEQUENCE: 44
gatgggagtc tg                                                       12

<210> SEQ ID NO 45
<211> LENGTH: 23
<212> TYPE: DNA
<213> ORGANISM: artificial sequence
<220> FEATURE:
<223> OTHER INFORMATION: cDNA of MiR-320a element

<400> SEQUENCE: 45
```

```
aaaagctggg ttgagagggc ggc                                              23

<210> SEQ ID NO 46
<211> LENGTH: 21
<212> TYPE: DNA
<213> ORGANISM: artificial sequence
<220> FEATURE:
<223> OTHER INFORMATION: cDNA of miR-320a element

<400> SEQUENCE: 46
aaaagctggg ttgagagggc g                                                21

<210> SEQ ID NO 47
<211> LENGTH: 22
<212> TYPE: DNA
<213> ORGANISM: artificial sequence
<220> FEATURE:
<223> OTHER INFORMATION: cDNA of miR-205 element

<400> SEQUENCE: 47
tccttcattc caccggagtc tg                                               22

<210> SEQ ID NO 48
<211> LENGTH: 22
<212> TYPE: DNA
<213> ORGANISM: artificial sequence
<220> FEATURE:
<223> OTHER INFORMATION: cDNA of miR-22 element

<400> SEQUENCE: 48
aagctgccag ttgaagaact gt                                               22

<210> SEQ ID NO 49
<211> LENGTH: 23
<212> TYPE: DNA
<213> ORGANISM: artificial sequence
<220> FEATURE:
<223> OTHER INFORMATION: cDNA of miR-221 element

<400> SEQUENCE: 49
agctacattg tctgctgggt ttc                                              23

<210> SEQ ID NO 50
<211> LENGTH: 22
<212> TYPE: DNA
<213> ORGANISM: artificial sequence
<220> FEATURE:
<223> OTHER INFORMATION: cDNA of let-7b element

<400> SEQUENCE: 50
tgaggtagta ggttgtgtgg tt                                               22

<210> SEQ ID NO 51
<211> LENGTH: 20
<212> TYPE: DNA
<213> ORGANISM: artificial sequence
<220> FEATURE:
<223> OTHER INFORMATION: cDNA of miR-744 element

<400> SEQUENCE: 51
tgcggggcta gggctaacag                                                  20

<210> SEQ ID NO 52
<211> LENGTH: 25
<212> TYPE: DNA
```

```
<213> ORGANISM: artificial sequence
<220> FEATURE:
<223> OTHER INFORMATION: cDNA of unknown element

<400> SEQUENCE: 52
aagctcaaga ataacgaaaa cggac                                       25

<210> SEQ ID NO 53
<211> LENGTH: 18
<212> TYPE: DNA
<213> ORGANISM: artificial sequence
<220> FEATURE:
<223> OTHER INFORMATION: cDNA of unknown element

<400> SEQUENCE: 53
ggtagcgtgg ccgagcgg                                               18

<210> SEQ ID NO 54
<211> LENGTH: 20
<212> TYPE: DNA
<213> ORGANISM: artificial sequence
<220> FEATURE:
<223> OTHER INFORMATION: cDNA of unknown element

<400> SEQUENCE: 54
gaagcgggtg ctcttatttt                                             20
```